United States Patent
Vergara et al.

(10) Patent No.: US 11,419,753 B2
(45) Date of Patent: Aug. 23, 2022

(54) THERMOELECTRIC TEMPERATURE CONTROLLED COOLER FOR BIOMEDICAL APPLICATIONS

(71) Applicant: THE REGENTS OF THE UNIVERSITY OF CALIFORNIA, Oakland, CA (US)

(72) Inventors: Julio L. Vergara, Los Angeles, CA (US); Andrew Padula, Laguna Nigel, CA (US); Lucas Restrepo, Scottsdale, AZ (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 150 days.

(21) Appl. No.: 15/715,395

(22) Filed: Sep. 26, 2017

(65) Prior Publication Data
US 2018/0098903 A1    Apr. 12, 2018

Related U.S. Application Data

(63) Continuation of application No. PCT/US2016/024501, filed on Mar. 28, 2016.
(Continued)

(51) Int. Cl.
*A61F 7/00* (2006.01)

(52) U.S. Cl.
CPC ............ *A61F 7/007* (2013.01); *A61F 7/0053* (2013.01); *A61F 7/0085* (2013.01);
(Continued)

(58) Field of Classification Search
CPC ... A61G 11/00; A61G 2210/70; A61F 7/0053; A61F 7/0085; A61F 7/007;
(Continued)

(56) References Cited

U.S. PATENT DOCUMENTS

| 2,991,627 A | 7/1961 | Suits |
| 3,196,524 A | 7/1965 | Jamison |

(Continued)

FOREIGN PATENT DOCUMENTS

| CA | 2980764 A1 | 10/2016 |
| CN | 101309657 A | 11/2008 |

(Continued)

OTHER PUBLICATIONS

ISA/US, United States Patent and Trademark Office (USPTO), International Search Report and Written Opinion dated Sep. 14, 2016, related PCT international application No. PCT/US2016/024592, pp. 1-13, with claims searched, pp. 14-17.
(Continued)

*Primary Examiner* — Kaitlyn E Smith
(74) *Attorney, Agent, or Firm* — O'Banion & Ritchey LLP; John P. O'Banion

(57) ABSTRACT

A heat exchanger module (HEM) and system uses a flexible substrate with one or more open channels, to which a substrate cover is bonded, thereby forming closed channels in the flexible substrate. Thermoelectric coolers (TECs) are attached to optional thermally diffusing copper squares atop the substrate cover. An interface cover is attached to the TEC tops, with a compliant thermally conductive material opposite the TECs and ultimately in contact with a patient. A liquid is passed through the closed channels, which act as thermal references for the TECs. Current is supplied by a controller to the TECs to induce TEC cooling or heating relative to the liquid. One or more temperature sensors detect the temperature of the interface cover, which are used as inputs to the control of the TEC supply current. The HEM may be used for heating, cooling, or cycling between heating and cooling for various medical uses.

19 Claims, 17 Drawing Sheets

FIG. 1D

Related U.S. Application Data

(60) Provisional application No. 62/139,676, filed on Mar. 28, 2015.

(52) U.S. Cl.
CPC ............ *A61F 2007/0075* (2013.01); *A61F 2007/0076* (2013.01); *A61F 2007/0086* (2013.01); *A61F 2007/0095* (2013.01)

(58) Field of Classification Search
CPC ...... A61F 2007/0075; A61F 2007/0076; A61F 2007/0078; A61F 2007/0086; A61F 2007/0093; A61F 2007/0095; F25B 21/02; F25B 2321/021; F25B 2321/023; H01L 35/30
See application file for complete search history.

(56) References Cited

U.S. PATENT DOCUMENTS

| | | |
|---|---|---|
| 3,867,939 A | 2/1975 | Moore |
| 4,470,263 A | 9/1984 | Lehovec |
| 4,846,176 A | 7/1989 | Golden |
| 4,860,748 A | 8/1989 | Chiurco |
| 4,962,761 A | 10/1990 | Golden |
| 5,097,829 A * | 3/1992 | Quisenberry ............. A61F 7/02 219/490 |
| 5,174,285 A | 12/1992 | Fontenot |
| 5,584,183 A | 12/1996 | Wright |
| 5,603,728 A | 2/1997 | Pachys |
| 5,653,741 A | 8/1997 | Grant |
| 5,800,490 A | 9/1998 | Patz |
| 5,871,526 A | 2/1999 | Gibbs |
| 5,887,435 A | 3/1999 | Morton |
| 5,895,418 A | 4/1999 | Saringer |
| 5,899,077 A | 5/1999 | Wright |
| 6,019,783 A | 2/2000 | Philips |
| 6,205,790 B1 * | 3/2001 | Denkin ............... G05D 23/1912 165/255 |
| 6,375,674 B1 | 4/2002 | Carson |
| 6,739,138 B2 | 5/2004 | Saunders |
| 6,764,502 B2 | 7/2004 | Bieberich |
| 6,840,955 B2 | 1/2005 | Ein |
| 7,022,093 B2 | 4/2006 | Smith |
| 7,077,858 B2 | 7/2006 | Fletcher |
| 7,637,263 B2 | 12/2009 | Fisher |
| 7,666,215 B2 | 2/2010 | Callister |
| 7,959,657 B1 | 6/2011 | Harsy |
| 8,065,763 B2 | 11/2011 | Brykalski |
| 8,192,474 B2 | 6/2012 | Levinson |
| 8,283,602 B2 | 10/2012 | Augustine |
| 9,078,478 B2 | 7/2015 | Ross, Jr. |
| 9,132,031 B2 | 9/2015 | Levinson |
| 9,192,474 B2 | 11/2015 | Forsell |
| 9,278,023 B2 | 3/2016 | Dabrowiak |
| 9,421,123 B2 | 8/2016 | Lee |
| 9,962,284 B2 | 5/2018 | Robinson |
| 10,292,859 B2 | 5/2019 | Levinson |
| 11,240,882 B2 | 2/2022 | Inaba |
| 2002/0026226 A1 | 2/2002 | Ein |
| 2002/0120317 A1 | 8/2002 | Fletcher |
| 2002/0156509 A1 | 10/2002 | Cheung |
| 2002/0161419 A1 | 10/2002 | Carson |
| 2003/0097845 A1 | 5/2003 | Saunders |
| 2004/0158303 A1 | 8/2004 | Lennox |
| 2004/0159109 A1 | 8/2004 | Harvie |
| 2005/0065581 A1 | 3/2005 | Fletcher |
| 2005/0143797 A1 | 6/2005 | Parish |
| 2006/0280948 A1 | 12/2006 | Moreshead |
| 2006/0293732 A1 | 12/2006 | Collins |
| 2008/0046047 A1 | 2/2008 | Jacobs |
| 2008/0077201 A1 | 3/2008 | Levinson |
| 2008/0077211 A1 * | 3/2008 | Levinson ............... A61F 7/0085 607/108 |
| 2008/0097560 A1 | 4/2008 | Radziunas |
| 2008/0097562 A1 | 4/2008 | Tan |
| 2008/0188915 A1 | 8/2008 | Mills |
| 2008/0249524 A1 | 10/2008 | Dunning |
| 2008/0287839 A1 | 11/2008 | Rosen |
| 2009/0000309 A1 | 1/2009 | Hershberger |
| 2009/0155838 A1 | 6/2009 | Hale |
| 2009/0264969 A1 | 10/2009 | Gammons |
| 2009/0312822 A1 | 12/2009 | Besner |
| 2010/0132930 A1 | 6/2010 | Izenson |
| 2010/0198322 A1 | 8/2010 | Joseph |
| 2010/0280581 A1 | 11/2010 | Cushman |
| 2011/0030754 A1 | 2/2011 | Smythe |
| 2011/0071603 A1 | 3/2011 | Moore et al. |
| 2011/0238050 A1 | 9/2011 | Allison |
| 2012/0118344 A1 | 5/2012 | Schluck |
| 2012/0239123 A1 | 9/2012 | Weber |
| 2013/0012388 A1 | 1/2013 | Song |
| 2013/0013033 A1 | 1/2013 | Lowe |
| 2013/0085552 A1 | 4/2013 | Mandel |
| 2013/0172829 A1 | 7/2013 | Badawi |
| 2014/0222121 A1 | 8/2014 | Spence |
| 2014/0228918 A1 | 8/2014 | Brienza |
| 2014/0276257 A1 | 9/2014 | Santa Maria |
| 2014/0311543 A1 | 10/2014 | Jinushi |
| 2014/0326287 A1 | 11/2014 | Wiant |
| 2014/0352325 A1 | 12/2014 | Brown |
| 2015/0080989 A1 | 3/2015 | Mohn |
| 2015/0223971 A1 | 8/2015 | Zaveri |
| 2015/0238349 A1 * | 8/2015 | Giuliani .................. A61F 7/00 602/2 |
| 2015/0366703 A1 * | 12/2015 | Du ..................... A61F 7/02 607/104 |
| 2016/0035957 A1 | 2/2016 | Casey |
| 2016/0178251 A1 | 6/2016 | Johnson |
| 2016/0270952 A1 | 9/2016 | Vergara |
| 2017/0027053 A1 | 1/2017 | Moczygemba |
| 2018/0204993 A1 | 7/2018 | Himmer |
| 2019/0099287 A1 | 4/2019 | Vergara |
| 2019/0099288 A1 | 4/2019 | Vergara |
| 2019/0262169 A1 | 8/2019 | Vergara |

FOREIGN PATENT DOCUMENTS

| | | |
|---|---|---|
| CN | 103142217 A | 6/2013 |
| CN | 203341808 U | 12/2013 |
| DE | 4238291 A1 | 5/1994 |
| DE | 202006020386 U1 | 7/2008 |
| EP | 3278047 A1 | 2/2018 |
| JP | H04077915 | 7/1992 |
| JP | H04077915 Y | 7/1992 |
| JP | 2003323219 | 11/2003 |
| JP | 2006230761 | 9/2006 |
| JP | 2006230761 A | 9/2006 |
| JP | 2008546510 A | 12/2008 |
| JP | 2009501067 A | 1/2009 |
| JP | 2010515481 | 5/2010 |
| JP | 2011067638 | 4/2011 |
| KR | 1020080060193 | 1/2008 |
| KR | 1020140140617 | 12/2014 |
| KR | 20150083559 A | 7/2015 |
| SU | 1179987 A1 | 9/1985 |
| TW | 201110282 A | 3/2011 |
| WO | 0195841 A2 | 12/2001 |
| WO | 0195841 A3 | 12/2001 |
| WO | 02064069 A2 | 8/2002 |
| WO | 2002064069 A2 | 8/2002 |
| WO | 2004111741 A1 | 12/2004 |
| WO | 2007005073 A2 | 1/2007 |
| WO | 2008039556 A1 | 4/2008 |
| WO | 2008039557 | 4/2008 |
| WO | 2008039557 A1 | 4/2008 |
| WO | 2008085162 A1 | 7/2008 |
| WO | 2011156643 A1 | 12/2011 |
| WO | 2013124866 A2 | 8/2013 |
| WO | 2013144008 A1 | 10/2013 |
| WO | 2014001789 A1 | 1/2014 |
| WO | 2014057450 A1 | 4/2014 |
| WO | 2015048170 | 4/2015 |

(56) References Cited

FOREIGN PATENT DOCUMENTS

| WO | 2015048170 A | 4/2015 |
|---|---|---|
| WO | 2015048170 A1 | 4/2015 |
| WO | 2016160691 | 10/2016 |
| WO | 2016160691 A1 | 10/2016 |
| WO | 2017171719 | 10/2017 |
| WO | 2017171719 A1 | 10/2017 |
| WO | 2017172836 | 10/2017 |
| WO | 2018064220 A1 | 4/2018 |
| WO | 2018064428 | 4/2018 |
| WO | 2018064428 A1 | 4/2018 |

OTHER PUBLICATIONS

IP Australia, Patent Examination Report 1 dated May 24, 2018, related Australian patent application No. 2014326780, pp. 1-4, with claims examined, pp. 5-7.
ISA/US, United States Patent and Trademark Office (USPTO), International Search Report and Written Opinion dated Aug. 28, 2017, related PCT international application No. PCT/US2017/024628, pp. 1-23, with claims searched, pp. 24-46.
ISA/US, United States Patent and Trademark Office (USPTO), International Search Report and Written Opinion dated Mar. 8, 2018, related PCT international application No. PCT/US2017/053812, pp. 1-16, with claims searched, pp. 17-35.
ISA/US, United States Patent and Trademark Office (USPTO), International Search Report and Written Opinion dated Feb. 6, 2018, related PCT international application No. PCT/US2017/054196, pp. 1-18, with claims searched, pp. 19-32.
IPEA/US, United States Patent and Trademark Office, International Preliminary Report on Patentability dated Mar. 8, 2019, related PCT international application No. PCT/US2017/024628, pp. 1-9, claims examined, pp. 10-34.
Korean Intellectual Property Office (KIPO), International Search Report and Written Opinion, counterpart PCT international patent application No. PCT/US2014/057276, dated Jan. 8, 2015, pp. 1-17, with claims searched, pp. 18-21.
European Patent Office (EPO), extended European search report dated Mar. 29, 2017, related European patent application No. 14849500.5, pp. 1-8, with claims searched, pp. 9-11.
ISA/US, United States Patent and Trademark Office (USPTO), International Search Report and Written Opinion dated Jul. 1, 2016, related PCT international application No. PCT/US2016/024501, pp. 1-19, with claims searched, pp. 20-25.
Japan Patent Office (JPO), official action dated Jul. 31, 2018, related Japanese patent application No. 2016-517424, Japanese-language document pp. 1-6, English-language translation pp. 7-12, claims examined pp. 13-16.
European Patent Office (EPO), Communication (Extended European Search Report) dated Oct. 18, 2018, related European patent application No. 16773916.8, pp. 1-9, claims searched, pp. 10-12.
IP Australia, Examination report No. 2 dated Dec. 6, 2018, related Australian patent application No. 2014326780, pp. 1-7, claims examined, pp. 8-11.
IPEA/US, United States Patent and Trademark Office (USPTO), International Preliminary Report on Patentability dated Sep. 10, 2018, related PCT international application No. PCT/US2016/024592, pp. 1-12, claims, pp. 13-20, drawings, pp. 21-46, Article 34 amendment, pp. 47-56.
Japan Patent Office (JPO), Decision of Refusal dated Dec. 11, 2018, related Japanese patent application No. 2016-517424, Japanese-language document pp. 1-6, English-language translation pp. 7-11, claims examined pp. 12-15.
IPEA/US, United States Patent and Tradmark Office (USPTO), International Preliminary Report on Patentability dated Oct. 21, 2019, related PCT international application No. PCT/US2017/054196, pp. 1-16, claims, pp. 17-45, Article 34 amendment, pp. 46-53.
European Patent Office (EPO), Communication (extended European search report) dated Sep. 25, 2019, related European patent application No. EP 16897277.6, pp. 1-9, claims searched, pp. 10-12.
European Patent Office (EPO), Communication (extended European search report) dated Oct. 22, 2019, related European patent application No. EP 17776506.2, pp. 1-12, claims searched, pp. 13-15.
Intellectual Property India, Examination Report dated Jan. 24, 2020, related India patent application No. 201647009683, pp. 1-6, claims examined, pp. 7-10.
Japan Patent Office (JPO), official action dated Apr. 21, 2020, related Japanese patent application No. 2016-517424, pp. 1-4, English-language translation pp. 5-8, claims examined pp. 9-12.
State Intellectual Property Office of the People's Republic of China, The Second Office Action dated Mar. 26, 2020, related Chinese patent application No. 201680019132.6, pp. 1-9, English-language translation, pp. 10-24, claims examined, pp. 25-32.
Japan Patent Office (JPO), official action dated Mar. 10, 2020, related Japanese patent application No. 2017-549684, pp. 1-5, English-language translation , pp. 6-10, claims examined, pp. 11-16.
Korean Intellectual Property Office (KIPO), official action dated Mar. 9, 2020, related Korean patent application No. 10-2017-7030302, pp. 1-7, English-language translation, pp. 8-10, claims examined, pp. 11-16.
Japan Patent Office (JPO), official action dated Mar. 17, 2020, related Japanese patent application No. 2018-550772, pp. 1-7, English-language translation, pp. 8-15, claims examined, pp. 16-19.
IP Australia, Examination report No. 1 for standard patent application dated Aug. 26, 2020, related Australian patent application No. 2016243565, pp. 1-5, claims examined, pp. 6-11.
National Intellectual Property Administration, PRC (CNIPA), The First Office Action dated Jul. 3, 2019, related China Patent Application No. 201680019132.6, Chinese-language document pp. 1-9, English-language translation p. 10-21, claims examined pp. 22-27.
European Patent Office (EPO), Communication (extended European search report) dated Apr. 8, 2020, related European patent application No. EP 17857465.3, pp. 1-8, claims searched, pp. 9-11.
Japan Patent Office (JPO), official action dated Jun. 16, 2020, related Japanese patent application No. 2019-074530, pp. 1-7, English-language translation (partial), pp. 8-12, claims examined, pp. 13-17.
Korean Intellectual Property Office (KIPO), official action dated Jun. 4, 2020, related Korean patent application No. 10-2018-7028057, pp. 1-4, English-language translation, pp. 5-7, claims examined, pp. 8-11.
State Intellectual Property Office of the People's Republic of China, The First Office Action dated Jul. 29, 2020, related Chinese patent application No. 201780020778.0, pp. 1-14, English-language translation, pp. 15-33, claims examined, pp. 34-58.
European Patent Office (EPO), Communication pursuant to Article 94(3) EPC dated Jun. 1, 2021, related European patent application No. 14 849 500.5, pp. 1-6, claims examined, pp. 7-10.
Korean Intellectual Property Office, Notice of Preliminary Rejection dated Jul. 16, 2021, related Korean patent application No. 10-2018-7028696, pp. 1-7, English-language translation, pp. 8-11, claims examined, pp. 12-24.
Japan Patent Office (JPO), official action dated Aug. 31, 2021, related Japanese patent application No. 2019-516508, pp. 1-6, English-language translation, pp. 7-12, claims examined, pp. 13-20.
IP Australia, Examination report No. 1 for standard patent application dated Feb. 21, 2022, related Australian patent application No. 2017335975, pp. 1-5, claims examined, pp. 6-19.
European Patent Office (EPO), Communication pursuant to Article 94(3) EPC dated Dec. 12, 2020, repated European patent application No. EP 16773916.8, pp. 1-8, claims examined, p. 9-10.
Canadian Intellectual Property Office, office action dated Dec. 29, 2020, related Canadian patent application No. 2,925,094, pp. 1-8, claims examined, pp. 9-12.
Japan Patent Office, official action dated Jan. 5, 2021, related Japanese patent application No. 2017-549684, pp. 1-4, English-language translation, pp. 5-7, claims examined, pp. 8-12.
IP Australia, Examination report No. 2 for standard patent application dated Aug. 26, 2020, related Australian patent application No. 2016243565, pp. 1-6, claims examined, pp. 7-11.

(56) References Cited

OTHER PUBLICATIONS

Korean Intellectual Property Office, official action dated Jan. 11, 2021, prepared Korean patent application No. 10-2016-7007807, pp. 1-11, English-language translation, pp. 12-14, claimls examined, pp. 15-18.

The Patent Office of the People's Repubic of China, official action dated Jan. 12, 2021, related Chinese patent application No. 2017800664983, pp. 1-6, Englis-language translation, pp. 7-15, claims examined, pp. 16-29.

State Intellectual Property Office of the People's Republic of China, The Third Office Action dated Feb. 28, 2022, related Chinese patent application No. 201780066498.3, pp. 1-3, English-language translation, pp. 4-8, claims examined, pp. 5-13.

State of Israel Ministry of Justice the Patent Authority, Notification No. 26, dated Dec. 1, 2021, related Israel patent application No. 265686, pp. 1-4, English-language translation, pp. 5-8, claims examined, pp. 9-19.

Japan Patent Office (JPO), official action dated Dec. 20, 2021, related Japanese patent application No. 2018-551821, pp. 1-3, English-language translation pp. 4-6, claims examined, pp. 7-35.

The Patent Office of the People's Repubic of China, official action dated Jan. 6, 2022, related Chinese patent application No. 201680084088.7, pp. 1-10, English-language machine translation, pp. 11-19, claims examined, pp. 20-23.

Korean Intellectual Property Office, official action dated Feb. 16, 2022, related Korean patent application No. 10-2019-7009157, pp. 1-7, English-language translation, pp. 8-11, claims examined, pp. 12-25.

Japan Patent Office (JPO), official action dated May 10, 2022, related Japanese patent application No. 2019-516508, pp. 1-3, English-language translation, pp. 4-6, claims examined, pp. 7-13.

Canadian Intellectual Property Office, office action dated May 27, 2022, related Canadian patent application No. 2,980,764, pp. 1-3, claims examined, pp. 4-9.

\* cited by examiner

THERMOELECTRIC TEMPERATURE CONTROLLED COOLER FOR BIOMEDICAL APPLICATIONS

CROSS-REFERENCE TO RELATED APPLICATIONS

This application is a 35 U.S.C. § 111(a) continuation of PCT international application number PCT/US2016/024501 filed on Mar. 28, 2016, incorporated herein by reference in its entirety, which claims priority to, and the benefit of, U.S. provisional patent application Ser. No. 62/139,676 filed on Mar. 28, 2015, incorporated herein by reference in its entirety. Priority is claimed to each of the foregoing applications.

The above-referenced PCT international application was published as PCT International Publication No. WO 2016/160,691 on Oct. 6, 2016, which publication is incorporated herein by reference in its entirety.

This application is related to PCT international application number PCT/US2014/057276 filed on Sep. 24, 2014, incorporated herein by reference in its entirety, which claims priority to, and the benefit of, U.S. provisional patent application Ser. No. 61/884,932 filed on Sep. 30, 2013, incorporated herein by reference in its entirety.

STATEMENT REGARDING FEDERALLY SPONSORED RESEARCH OR DEVELOPMENT

This invention was made with Government support under AR047664 and AR054816, awarded by the National Institutes of Health. The Government has certain rights in the invention.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to Peltier devices, and more particularly to flexible thermoelectric coolers that may also be used for heating.

2. Background Discussion

Currently, hypothermia treatment of brain injuries, spinal cord injuries, muscles or joint injuries is typically afforded by using ice packs or chemical cool packs that provide incomplete and short-lived cooling. For more advanced treatments, it would appear that the only products presently available use pads or cold caps that cool using circulating water, which is typically set at around 4° C. to 7° C. These devices, though better than passive cooling, have four major deficiencies:

(a) They utilize water chillers or refrigerators that must cool a significant volume of water (gallons) for their reliable operation, since water is the cooling agent used to cool or heat human tissue. This creates several technical limitations, most significantly the inability to effectively control the patient's tissue temperature. These devices have problems with overshooting and undershooting their target temperatures.

(b) By circulating chilled water, these devices are prone to water condensation and heat transfer to the environment that limits their efficiency.

(c) For the most part, these devices are bulky, not portable, and must be permanently connected to an AC power outlet for their operation.

(d) These devices cannot be readily utilized in ambulances and cannot be offered as initial treatment devices in adult emergencies.

BRIEF SUMMARY

A heat exchanger module (HEM) and system uses a flexible substrate with one or more open channels, to which a substrate cover is bonded, thereby forming closed channels in the flexible substrate. The resulting closed channels may be used to pass a liquid to broadly control temperatures in structures in thermal contact with the flexible substrate.

Thermoelectric coolers (TECs) are attached to optional thermally diffusing copper squares atop the substrate cover. An interface cover is attached to the TEC tops, with a compliant thermally conductive material opposite the TECs and ultimately in contact with a patient.

The liquid that is passed through the closed channels acts as thermal references for the TECs. Current is supplied by a controller to the TECs to induce TEC cooling or heating relative to the liquid. The liquid may be deionized water, deionized water with one or more additives to increase cooling performance, operational temperature zone, or corrosion properties, or another fluid with thermal conductivity properties comparable or better than deionized water.

One or more temperature sensors detect the temperature of the interface cover, which may be used as inputs to the control of the TEC supply current. The HEM may be used for heating, cooling, or cycling between heating and cooling for various medical uses.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings, which are for illustrative purposes only.

DETAILED DESCRIPTION

A heat exchange system according to the technology of this disclosure generally comprises: (1) one or more heat exchanger modules, and (2) a controller.

1. The Heat Exchanger Module (HEM)

Figure 1A:
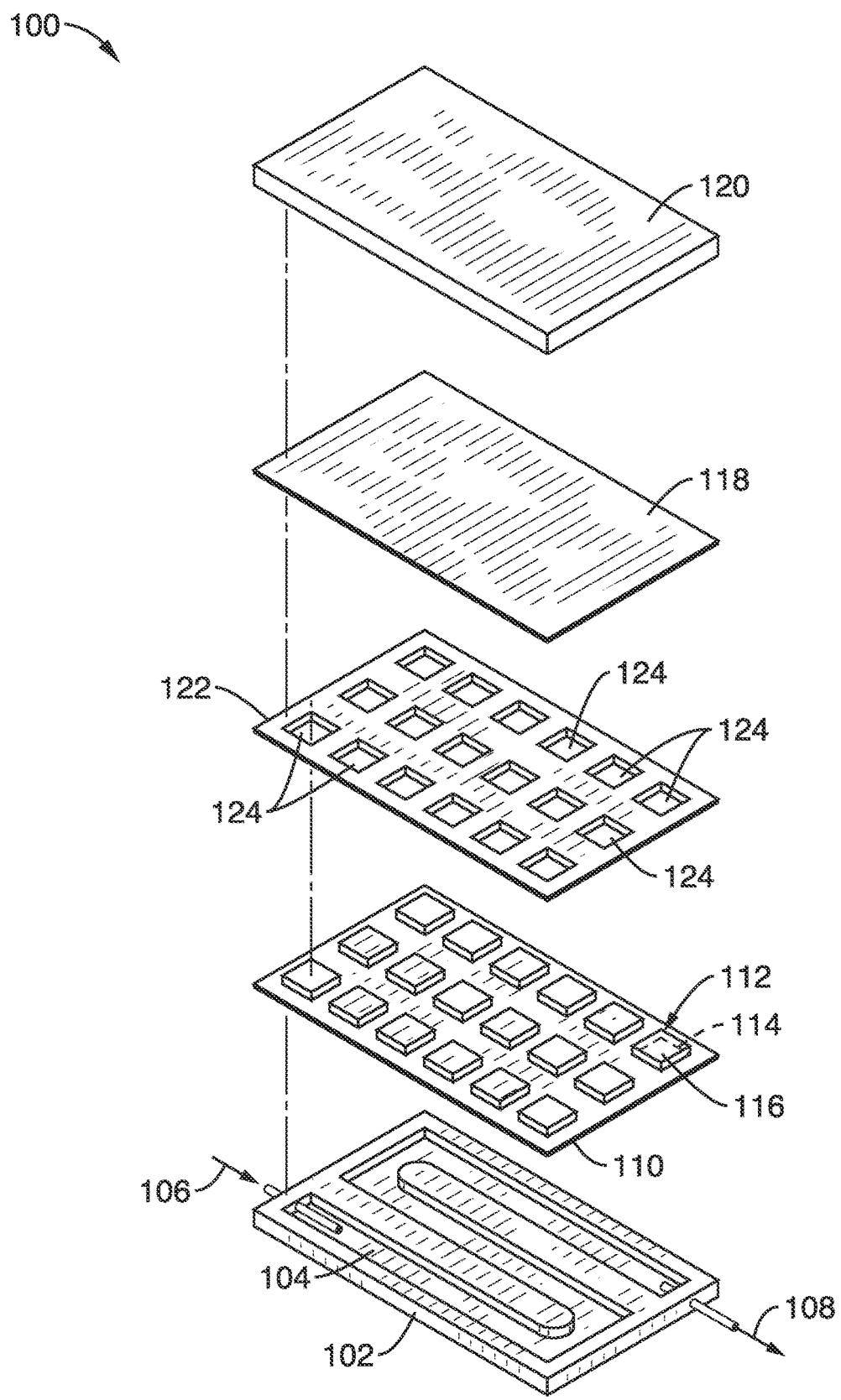
FIG. 1A is an exploded perspective view of a heat exchanger module (HEM) comprising 18 thermoelectric coolers (TECs).

Refer now to FIG. 1A through FIG. 1D. FIG. 1A is an exploded perspective view of a heat exchanger module (HEM) 100. Each HEM 100 typically comprises a flexible substrate 102 comprising a molded open channel 104 that will be subsequently used for fluid circulation. The open channel 104 has a fluid input 106 and fluid output 108 whereby the fluid is used for heat transfer. The flexible substrate 102 is in turn bonded to a substrate cover 110.

The substrate cover 110 has a high thermal conductance, and may be selected from materials consisting of copper (with thermal conductivity of approximately 400 W/m*K), brass (with thermal conductivity of approximately 120 W/m*K), aluminum (with thermal conductivity of approximately 385 W/m*K), or pyrolytic graphite sheets (with thermal conductivity of approximately 600-800 W/m*K), or other thermally conductive synthetic materials. The high thermal conductance may also be achieved by using thinner materials with relatively lower thermal conductivity, or by a combination of one or more of the foregoing.

The term "cover" may, without limitation, also include a foil. Such foils can be copper, brass, aluminum, stainless steel, or other heat conductive materials such as carbon fiber composites; their thickness can range from approximately 100 μm to approximately 635 μm.

Attached to the substrate cover 110 are one or more thermoelectric coolers (TECs) 112. In FIG. 1A, 18 such TECs 112 are shown; however, there may be either more or fewer TECs 112. In operation, each TEC 112 has a reference side 114 and an oppositely disposed patient side 116. In the FIG. 1A example, a reference side 114 of the TECs 112 is bonded (using thermally conductive adhesive) to the other substrate cover 110 to create a heat sink.

The patient side 116 of the TECs 112 are bonded to an interface cover 118. The interface cover 118 may be coated with soft thermally conductive elastomer 120. The soft elastomer 120 would act as a protective interface between the patient's skin (not shown) and the interface cover 118.

Figure 1B:
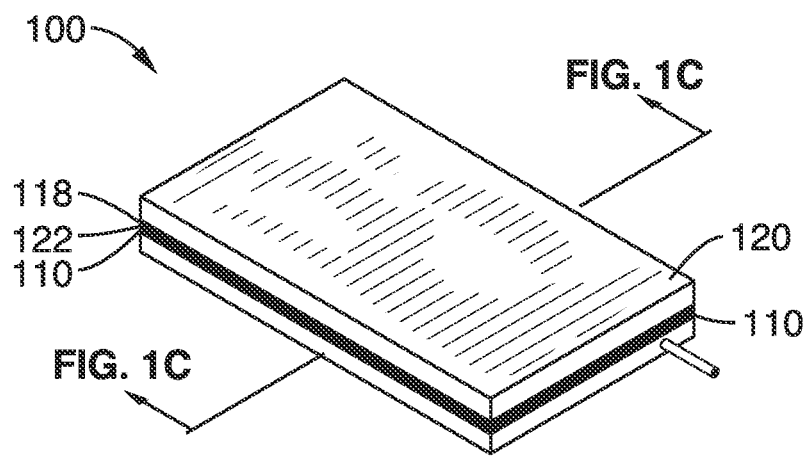
FIG. 1B is an assembled perspective view of the heat exchanger module (HEM) that has been assembled from the exploded components of FIG. 1A.
Figure 1C:
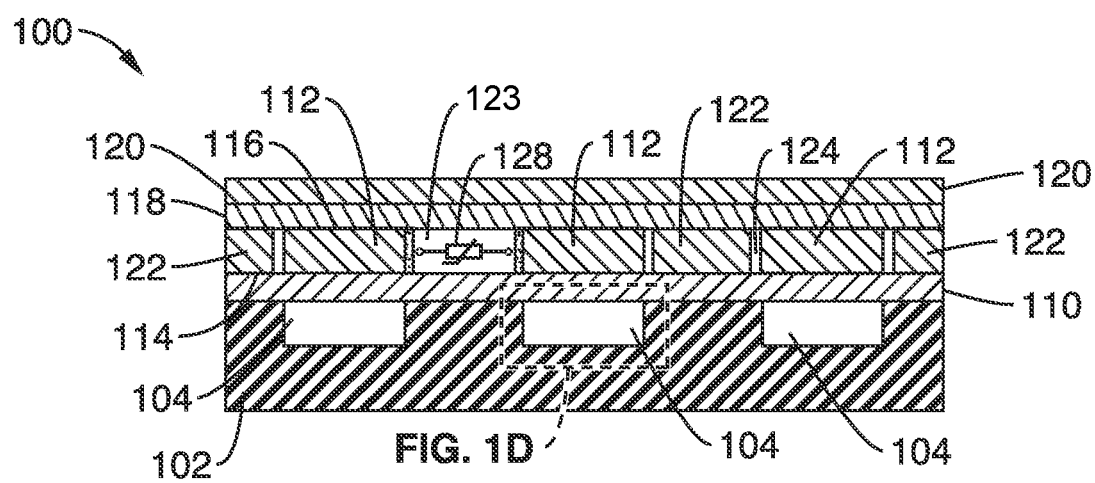
FIG. 1C is a cross section of the assembled heat exchanger module (HEM) of FIG. 1B.

An interstitial gap 123, as shown in FIG. 1C, is formed between the substrate cover 110 and the interface cover 118 by the thickness of the TECs 112. The interstitial gap 123 between the various TECs 112 may be filled with thermal insulation material (e.g. polyurethane or silicone foam, or spun polyester). In the case of a preformed interstitial gap insulating material 122, a device gap 124 for each TEC 112 would exist to allow placement over the TECs 112.

The heat exchanger module 100 uses thermoelectric coolers 112 as direct cooling or heating agents to create normothermia, hypothermia, or hyperthermia in a patient. The TECs 112 would typically function as Peltier devices, operating as solid state refrigeration devices passing heat from the reference side 114 to the oppositely disposed patient side 116 upon application of an applied electrical current. While the TECs 112 are generally used as cooling devices, they may also be used as heating devices by reversal of the applied electrical current.

FIG. 1B shows an assembled perspective view of the heat exchanger module (HEM) that has been assembled from the exploded components of FIG. 1A.

FIG. 1C shows a cross section of the assembled heat exchanger module (HEM) of FIG. 1B, pointing out the various component comprising the HEM 100 of FIG. 1B. In the figure a thermistor 128 is shown retained in an interstitial gap 123 which does not contain any thermal insulation material.

Figure 1D:
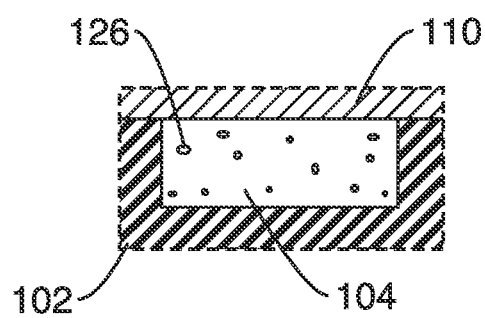
FIG. 1D is a cross section detail of one of the closed channels of FIG. 1C.

Looking more particularly to FIG. 1D, when the flexible substrate 102 is bonded to the substrate cover 110, the open channel 104 is in turn closed, forming a closed channel 126, whereby the fluid input 106 of FIG. 1A passes through the closed channel 126, exiting through the fluid output 108 of FIG. 1A.

The closed channel 126 formed by the bonding of the flexible substrate 102 to the substrate cover 110, allows passage of a heat transfer fluid to operate either as a heat sink or heat source, essentially providing a thermal reference for the operation of the TECs 112. For convenience, and for this reason, the reference side 114 of the TECs 112 are adjacent to the thermal reference fluid that flows through the closed channel 126.

When the TECs 112 are operated in cooling mode, heat is passed from the soft thermally conductive elastomer 120, through the interface cover 118, through the TECs 112 from the patient side 116 to the reference side 114, through the substrate cover 110, and ultimately to the fluid passing through the closed channel 126. The fluid passing through the closed channel 126 may be water at, above, or below, room temperature water for thermal reference operation.

In one embodiment, the heat exchanger module 100 flexible substrate 102 may be molded in silicone or other low durometer plastic material to better conform to various body parts or tissues. The heat exchanger module 100 may be shaped as flat or curved units as further described below.

Since the natural flow of heat is always from hot to cold, the overall process of heat extraction from a patient's skin occurs when DC power is applied to the TECs 112; their "cold" patient side 116 becomes colder than the patient's skin allowing heat to flow from the patient's skin through the TECs 112 to the fluid passing through the closed channel 126.

The water flowing through the closed channel 126 ensures that heat flows naturally from the substrate cover 110 to the water without major temperature increases. The end result is that the patient's skin temperature is lowered in a controlled fashion.

2. The Interface Cover in the Heat Exchanger Module

Referring once again to FIG. 1C, a layer of soft thermally conductive elastomer 120 is applied to the interface cover 118 as well as a layer of insulation between the two plates within the interstitial gap 123.

The layer of soft thermally conductive elastomer 120 acts a buffer between the body tissue and interface cover 118 so that the body is not in direct contact with the interface cover 118.

The composition of the soft thermally conductive elastomer 120 is typically, but not necessarily, a combination of two conductive silicones. In one present embodiment the soft thermally conductive elastomer 120 is comprised of about 50% silicone A (Insulcast 3-95-2) and about 50% silicone B (Dow Corning Toray SE 4430).

The soft thermally conductive elastomer 120 mixture is spread over the interface cover 118, creating a layer as thin as possible while completely covering any exposed metal of the interface cover 118. The interface cover 118 with the soft thermally conductive elastomer 120 is then set in an oven for 30 minutes at 120° C. When removed from the oven, any excess silicone is trimmed from the interface cover 118 using a razor blade.

3. Interstitial Gap Insulation in the Heat Exchanger Modules

Referring once again to FIG. 1C, an interstitial gap 123 is formed between the interface cover 118 and the substrate cover 110. This interstitial gap 123 may be partially or completely filled with an insulating layer.

One purpose of the insulating layer in the interstitial gap 123 is to provide structural support to the HEM 100, while minimizing heat transfer between the substrate cover 110 and the interface cover 118. Such heat transfer between the substrate cover 110 and the interface cover 118 would severely diminish the efficiency of the overall HEM 100. While air may be a better insulator than insulation in the interstitial gap 123, the interface cover 118 would very quickly warp due to a lack of support.

In one present embodiment, the insulating foam disposed in the interstitial gap 123 is Smooth-On Flex Foam-It III. This two-part foam is mixed in a ratio of 57.5:100 of parts A and B by weight, respectively. Part B is generally weighed first. Part A is then quickly weighed, added to part B, and the two mixed together. The Part A and B mixture is then stirred quickly and vigorously for a few seconds and poured into a syringe (not shown).

The syringe is used to inject the foam into the interstitial gap 123 between the interface cover 118 and the substrate cover 110, allowing the foam to expand outward. A piece of plastic wrap is wrapped around the HEM 100 to prevent over expansion of the foam out of the device.

After allowing the foam in the interstitial gap 123 to cure for one hour, the plastic wrap is removed and any excess foam is trimmed away.

4. The Heat Exchanger Module System

Figure 2:
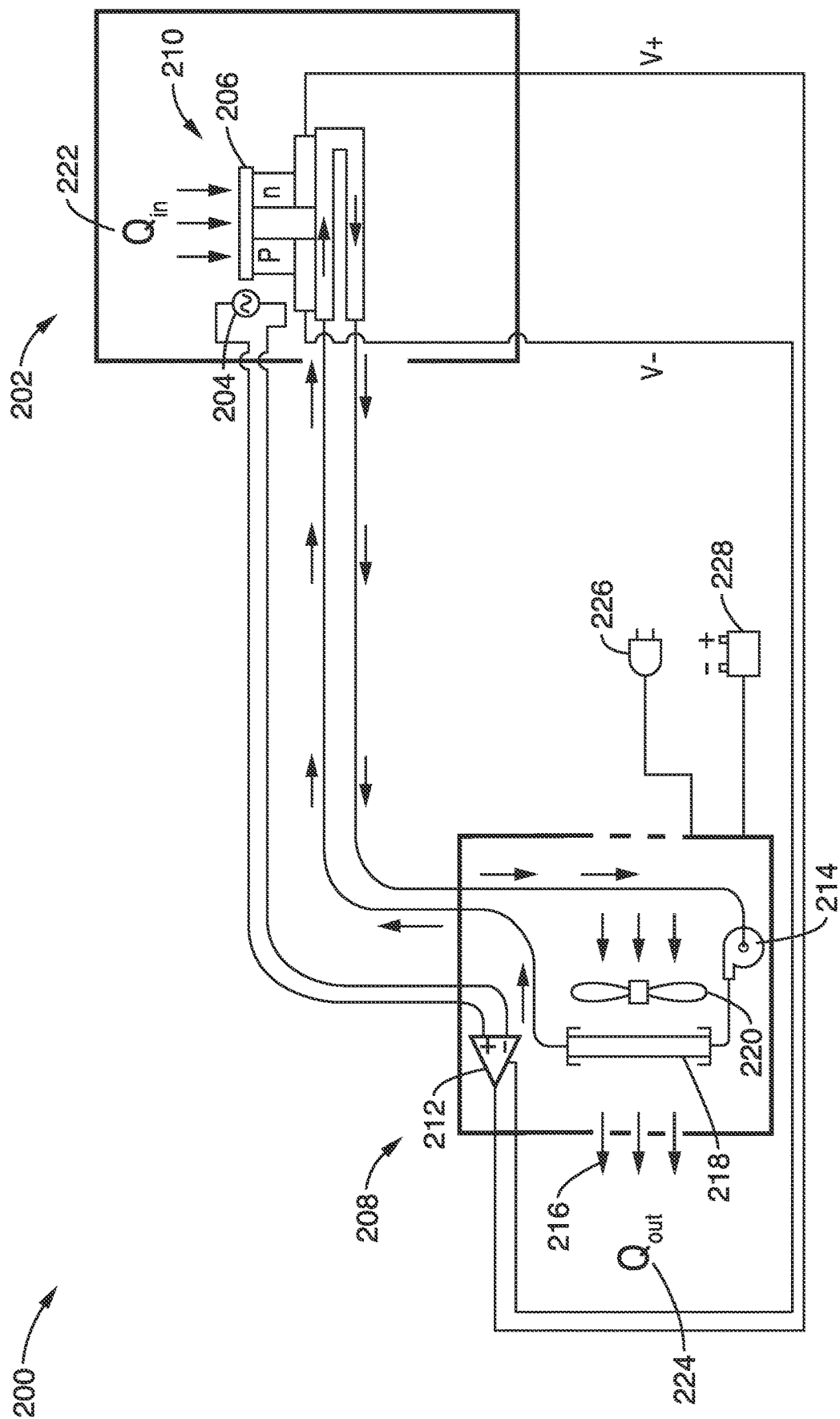
FIG. 2 is a simplified overview of a heat exchanger module (HEM) and a system controller, with interconnections shown.

Refer now to FIG. 2, which is an overview of a heat exchanger module (HEM) system 200 with interconnections shown. An HEM 202 may be built with one or more embedded temperature sensors 204 (thermistors or thermocouples) that constantly monitor the interface cover 206 in the interstitial gap 123 shown in FIG. 1C, thereby providing a reliable indication of the patient skin temperature (through the soft thermally conductive elastomer 120 previously shown in FIG. 1C). These embedded temperature sensors 204 provide feedback for the electronic servocontrol unit (or controller 208 for short) that drives the TECs 210 using a proportional-integral-derivative (PID) or equivalent servo controller 212 and a pulse width modulation ("PWM") or analog DC power supply module (here, shown as included in the PID controller 212 as a simple gain block amplifier).

The heat exchange is accomplished by the HEM system 200 by flowing (by use of a pump 214) a heat exchange medium (typically water) through the TECs 210 and dissipated 216 to ambient air through the use of a heat exchanger 218 in the controller 208. Depending on the configuration of the controller 208, a fan 220 may be used to force air through the heat exchanger 218, or the heat exchanger may be a passive (typically finned) water-to-air design (not shown).

The portable closed-loop ambient temperature water (or liquid coolant) circulator (0.5-3 L/min) and radiator that allows for up to 1 kW heat dissipation to the air with temperature differences not exceeding 10° C. The total volume of circulating liquid in the closed loop system is given by the sum of: a) the inner volume of connecting hoses; b) the volume of HEMs water channels; c) the volume of water in the radiator; and, d) the volume of a small accessory water reservoir.

Each HEM system 200 is capable of extracting heat from (or providing heat to) human skin at a flux rate that is 10-50-fold the steady state heat generation capacity of various human organs. These heat transfer values for the adult brain range from <0.01 W/cm² to ~0.04 W/cm² as calculated for an average adult at rest and then under deep stress or exercise conditions. Ultimately, the HEM system 200 transfers heat $Q_{in}$ 222 from the patient to the ambient air as $Q_{out}$ 224.

As previously shown in FIG. 1A through FIG. 1E, to achieve heat transfer densities of between 0.1-2 W/cm², multiple TEC 112 elements may be combined into molded units that ultimately interface with the skin through the soft thermally conductive elastomer 120.

Now referring back to FIG. 2, the PID controller 212 electronic power module manages the power delivery to the TECs 210 with a high current H-Bridge or other high current source. The power modules may be implemented either by using DAC interfaces under proprietary program control, or programmable modules using proprietary code written in machine code. These modules optimize the HEM system's 200 performance in order to reach the desired (set) human skin contact temperature in a stable fashion in the shortest possible time by incorporating standard parameter optimization (tuning) routines.

Power to the TECs 210 is controlled according to cooling/heating paradigms customized for specific treatments.

In operation, the HEM system 200 uses an operator interface (not shown) such as a touch screen control graphic panel with the functionality to: a) read and set temperatures; b) start or stop complex cooling or heating profiles; b) define the upper and lower limits for the cooling and heating ranges, which are typically 60° C. and 6° C., respectively; c) access routines to optimize PID parameters; d) access routines to program fluid and heat exchange rates; e) select between AC or battery operation; e) graphically display temperature plots; and, f) access an emergency button to halt the cooling or heating operation of the HEM system 200.

A more comprehensive set of functions to control the ESU would be attained by a wireless computer interface (also not shown) that includes the possibility to download the data for medical documentation.

Operation of the HEM system 200 could also be at low voltages (12 or 24V) and could be powered by a battery, which will be shown below.

5. Channels Disposed in the Heat Exchanger Modules

Figure 3A:
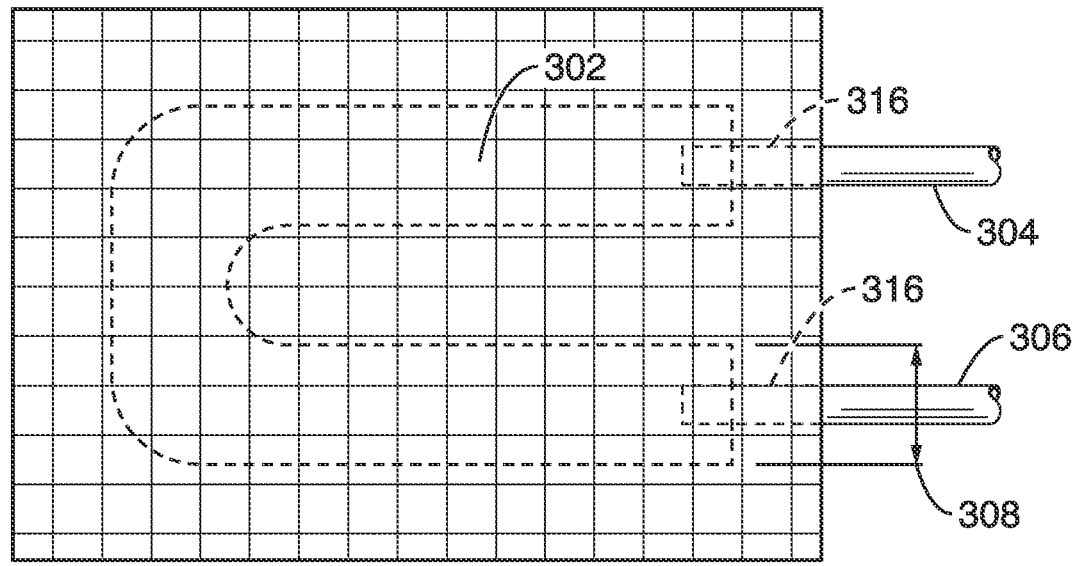
FIG. 3A is a top view of a thermoelectric cooler electrical channel disposed in a flexible substrate, where the channel will be used for transferring a heat transfer medium.
Figure 3B:
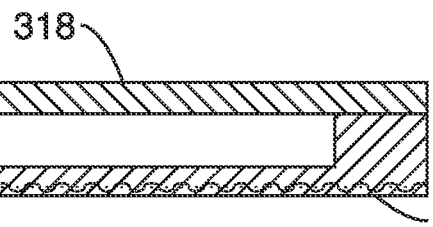
FIG. 3B is a cross section of the flexible substrate of FIG. 3A.

Refer now to FIG. 3A and FIG. 3B, which show more details of the channel used to provide for circulation of a heat exchanger liquid. Typically, the flexible substrate 300 has one or more open channels 302 that are molded into it. Each channel 302 has provisions for a liquid input 304 and liquid outlet 306, whereby the heat exchanger fluid is passed through the channel 302.

In this FIG. 3A, the flexible substrate 300 is shown, without the closure of the open channel 302 into a closed channel that was previously described above in FIG. 1D as element 126.

The open channel 302 is typically molded into silicone to allow for flexibility as the heat exchanger module is pressured against body tissues during operation.

Each open channel 302 is based on the requirements of the individual cooler. The width 308 of the channel 302 as well as the depth 310 of the channel 302 in the overall thickness 312 of the flexible substrate 300 varies between each cooler, but there are some important requirements that would likely be met:

(1) The flexible substrate 300 should be sufficiently reinforced so as to prevent ballooning of the channel 302 under operating pressure. A reinforcement mesh 314 may be used for this purpose. The mesh 314 may be chosen for flexibility as well as good shear strength to prevent bulging of the channel 302 under pressurized conditions. The mesh 314 may be placed inside the silicone during the pouring process so that it is thereby embedded in the silicone.

(2) The wall height 310 of the channel 302 should allow for sufficient water flow (typically 0.0833-0.05 L/s). There may be series and parallel channels (not shown) utilized to accomplish this volume of flow.

(3) The width 308 of the channel 302 should be sufficiently narrow so as to allow for adhesion the substrate cover (described in FIG. 1C as element 110).

(4) The width 308 of the channel 302 should be designed for the intended operational water pressure, and should typically match the width of the TECs (not shown) being used, thereby maximizing heat transfer from the TECs to the fluid flowing in the channel 302.

(5) Frames used to build the flexible substrate 300 and the inserts that displace that form the channel 302 may be created by either laser cut acrylic plastics or a 3D printer based on 3D graphic designs using commercial software.

(6) Inlet and outlet attachment holes 316 may either be molded in, or cut into the flexible substrate 300 channel 302 by using a biopsy. After successfully attaching the flexible substrate 300 to the substrate cover 318, nylon or silicone tubing may be glued into the attachment holes using flexible cement, with the tubing acting as a liquid inlet 304 and liquid outlet 306. Alternatively, the attachment holes 316 may be smaller channels (not shown) themselves with tubing flattened with a vise attached to form alternate inlets or outlets.

6. Covers in the Heat Exchanger Modules

Refer back to FIG. 1C to better view the substrate cover 110 and interface cover 118. The purpose of these two high thermal conductivity covers is to attempt to create a uniform temperature surface (i.e. to minimize temperature gradients) on either side of the TECs 112 for heat extraction on the patient side 116 and dissipation on the reference side 114. In one embodiment, the substrate cover 110 and interface cover 118 may be copper or other high thermal conductivity material.

As the interface cover 118 is bonded to a soft biocompatible elastomer 120 in direct contact (not shown) with a patient's skin, the substantially uniform cooling or heating is effected on the body tissues.

Similarly, the substrate cover 110 facilitates heat transfer to the heat transfer liquid flowing in the closed channel 126.

The thicknesses of the substrate cover 110 and interface cover 118 should be minimized to reduce weight and improve flexibility, but still should be thick enough to provide support to the TECs 112. For example, in current embodiments, thickness ranges from 127-203.2 μm.

The substrate cover 110 and interface cover 118 may be cut to a specific size with a guillotine paper cutter and then flattened by rolling. They may then be sanded using 50 grit sandpaper to help flatten them, as well as promote subsequent adhesion. The sanded covers are then rinsed with water, cleaned with acetone, and finally rinsed again with distilled water.

Figure 4A:
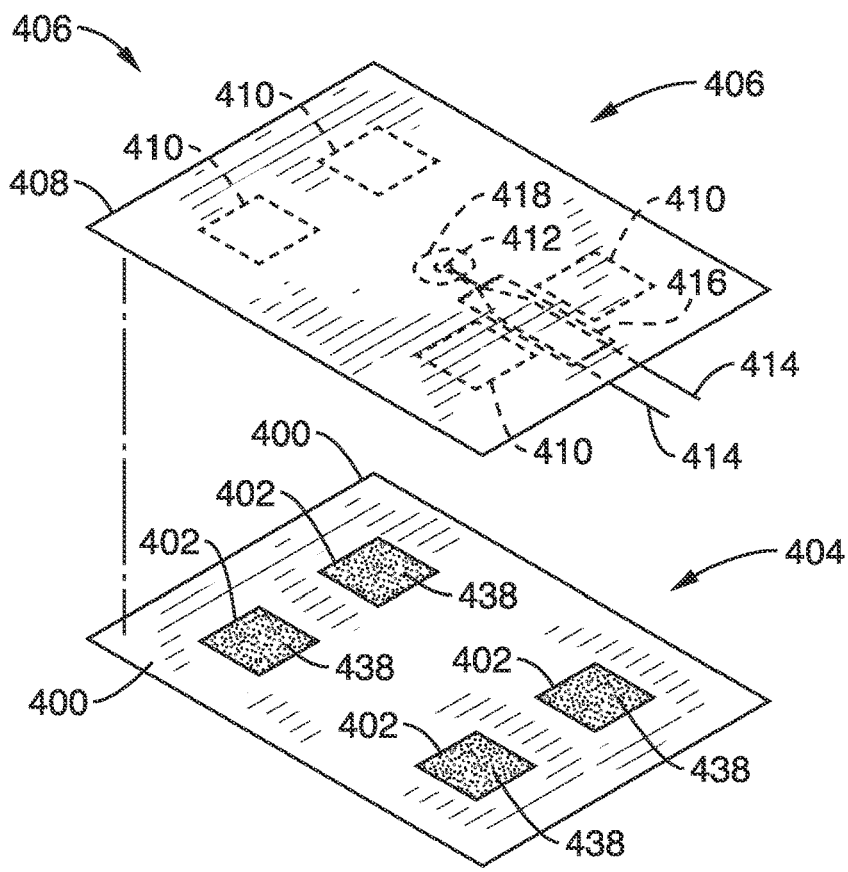
FIG. 4A is a perspective view of a substrate cover with copper squares, and an interface cover disposed above.
Figure 4B:
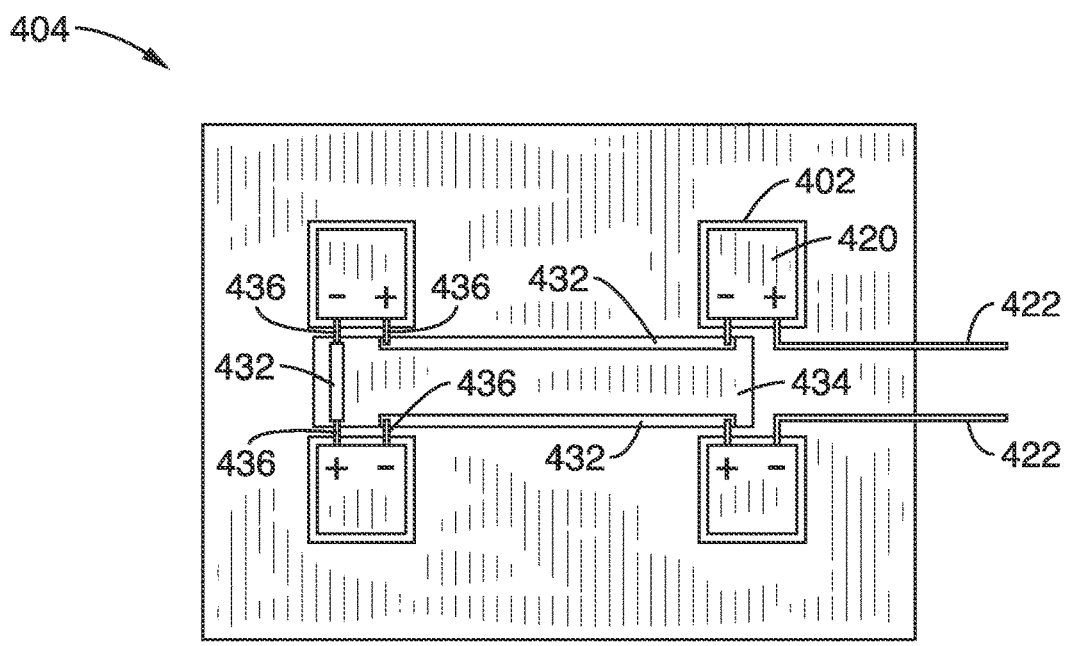
FIG. 4B is a top view of the substrate cover with the thermoelectric coolers wired.
Figure 4C:
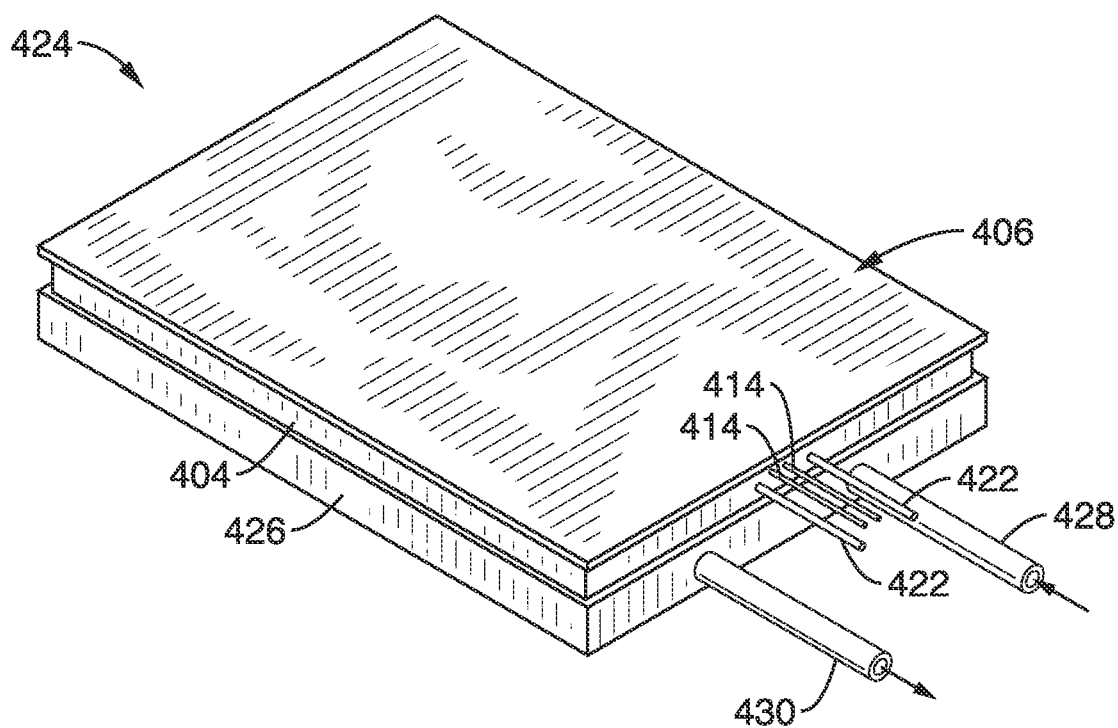
FIG. 4C is a perspective view of the substrate cover and interface covers of FIG. 4A completed into a heat exchanger module (HEM) with insulation between the substrate cover and the interface cover.

Refer now to FIG. 4A through FIG. 4C. Here, the lower substrate cover 400 has mounted upon it four copper squares 402 in an orderly fashion at places where the TECs (not shown) will be positioned in the future. These copper squares 402 act as reinforcements to the lower substrate cover 400 that prevent bending around the TECs (not shown).

The copper squares 402 may be of similar thickness or thicker than the substrate cover 400, and may be cut with a guillotine paper cutter, stamp, laser, or other cutting method. The copper squares 402 may be flattened by rolling to ensure they are sufficiently flat. They may then be sequentially sanded with 50 grit sand paper, cleaned with acetone, and rinsed with distilled water.

In one embodiment, the copper squares 402 may be bonded to the substrate cover 400 in a reflow soldering oven using lead-free RoHS compliant eutectic paste (not shown). The positions of the squares are previously demarcated with a thermally resistant tape that also prevents solder from flowing from beneath the copper squares 402. A thin layer of solder paste is then applied to the substrate cover 400 (enough so the plate cannot be seen) and squares may then be pressed into the solder paste.

It should be noted that the copper squares 402 act as thermal diffusers, maintaining a substantially constant temperature within them due to their high thermal conductivity. It is apparent that the copper squares 402 could be omitted by increasing the thickness of the substrate cover 400.

The cover assembly 404 of the substrate cover 400, solder (not shown), and copper squares 402 may then be placed into an oven that reaches a temperature of roughly 245° C., allowing the solder to reflow. The oven may then reduce the assembly temperature in a controlled manner.

Once the cover assembly 404 has cooled, it is cleaned first with acetone to remove remaining solder flux and residue. It is then cleaned with diluted sulfuric acid (approximately 10%) to remove oxidation and residue. The cover assembly 404 is then rinsed with acetone and distilled water to complete the cleaning.

In a similar fashion, an interface assembly 406 comprising an interface cover 408 and copper squares 410 may be constructed, soldered together, and cleaned.

After the interface assembly 406 is completed, a thermistor 412 with lead wires 414 is added to measure the cold side temperature of the cooler. To do this, the thermistor 412 is placed in a suitable location and the lead wires 414 are taped 416 to the interface cover 408 using thermally resistant tape. A thermally conductive adhesive 418 is then placed around the thermistor 412, just enough to cover it completely. The interface assembly 406 is then placed in an oven for 30 minutes at 120° C. to cure the thermally conductive adhesive 418 and set the thermistor 412 in place.

In FIG. 4B, the cover assembly 404 is shown with the TECs 420 mounted to the copper squares 402, and wired in series with exiting leads 422.

In FIG. 4C, a completed Heat Exchanger Module 424 is shown, where the cover assembly 404 has been mounted to a flexible substrate 426, the interface assembly 406 has been bonded to the top of the TECs 420 (not seen in this view), and thermal insulation has been applied to the interstitial gap between the cover assembly 404 and the interface assembly 406. The thermistor 412 (not seen in this view) lead wires 414 are seen exiting the HEM 424, along with the TEC 420 (not seen in this view) wiring 422. Finally, the coolant inlet 428 and outlet 430 tubes are seen. As previously discussed above, the coolant inlet 428 and outlet 430 tubes connect to closed channels formed within the flexible substrate 426 to provide a reference temperature for the TECs 420 (not seen in this view).

7. Thermoelectric Coolers (TECs) for Heat Exchanger Modules (HEMs)

In FIG. 4B, the thermoelectric coolers 420 (TECs) are important components that drive the cooling in the heat exchanger module 424 (HEM). Since TECs 420 are available in many sizes and wattages, each HEM 424 utilizes either a single TEC 420, or arrays of TECs organized into patterns that optimize heat transfer according to requirements of each specific target tissue to be cooled.

Typically, TECs 420 of the same size and power are always chosen for each HEM 424.

The TECS 420 may be optimized into configurations that are connected in series, parallel, or in series and parallel combinations, so that the combined voltage requirement matches that delivered by the controller (typically 12 or 24V) current source.

In current embodiments for 12V current sources, the TEC 420 layouts consist of multiple banks of 3 TECs with each TEC rated at 4 volts, banks of 2 TECs rated at 6 volts each, or banks of 4 TECs 420 rated at 3 volts each (as shown in FIG. 4B). Multiple alternative combinations are envisioned for either 12V or 24V units.

In designs having multiple banks of TECs, the electrical current demand increases significantly for each bank added. To minimize heat generation, hefty copper bus power lines 432 may be used to replace most of the wiring between TECs 420. The copper bus power lines 432 may be insulated from the generally electrically conductive substrate cover 400 by way of an electrically insulated tape or an otherwise electrically insulated region 434.

The overall power draw of each HEM 424 is determined by its size (total area covered) and heat transfer design capacity. In general, an HEM 424 is designed to have an average heat transfer of ≥0.5 W/cm$^2$ of body tissue contact.

After determining an appropriate TEC 420 layout, the TECs are prepared for adhesion to the bottom metal plate using the following process:

(1) The wires on each TEC 420 are trimmed down to <6.2 cm, with the exception of the exiting leads 422, which ultimately connect to an external power supply.

(2) Copper bus lines 432 are cut to the corresponding lengths between TECs 420, and the TEC 420 wires 436 are each soldered with RoHS lead-free solder to the bus lines 432. If the cooler has multiple banks, the bus lines 432 are soldered together at junctions.

(3) Each TEC 420 is cleaned with acetone upon completion of soldering.

(4) To prevent short circuits, insulating tape 434 is placed on the substrate cover 400 in any area where the bus lines 432 may come into electrical contact.

(5) Referring back to FIG. 4A, a thin layer of thermally conductive adhesive 438 is spread onto each copper square on the substrate cover 400. Each of TECs 420 is then placed on top of the respective thermally conductive adhesive 438, followed by weights on top of the TECs 420 to compress the thermally conductive adhesive 438 into a thin layer. The cover assembly 404 is then placed in the oven at 120° C. for 60 minutes to cure.

(6) After curing, a similar thermally conductive adhesive (not shown) is then applied in another thin layer to the top surface of each of the TECs 420. The interface cover 406, with a thermistor 412 previously attached (as described above) is then placed on top of the TECs 420 followed by weights. The cooler is again placed in the oven at 120° C. for 60 minutes to cure.

8. Substrate Cover to Flexible Substrate Bonding to Provide Closed Channels in the Heat Exchanger Modules Refer now to FIG. 5A through FIG. 5D. Here, a bonded substrate assembly is shown 500, where a flexible substrate 502 has been bonded to a substrate cover 504. The interface between the substrate cover 504 and the flexible substrate 502 requires sufficient adhesion to prevent coolant leakage when the closed channels 506 are pressurized. Three methods have been developed to attach the silicone of the typical flexible substrate 502 to the metal of the typical substrate cover 504.

As a common initial step, all methods require preparing the substrate cover 504 surface metal to promote adhesion. This is accomplished by:

(1) Sanding the substrate cover 504 using rough sandpaper (<50 grit);

(2) Degreasing the substrate cover 504 using acetone or other solvent, and (3) Coating the substrate cover 504 with a primer.

8.1 Method 1

This method involves gluing the silicone flexible substrate 502 directly to the metal of the substrate cover 504. This process is one of the simplest solutions of this attachment problem.

(1) Initially, the attachment face 508 of the substrate cover 504 to be glued to the flexible substrate 502 is coated with a primer (not shown) and then placed in an oven at 60° C. for one hour to cure.

Figure 5A:
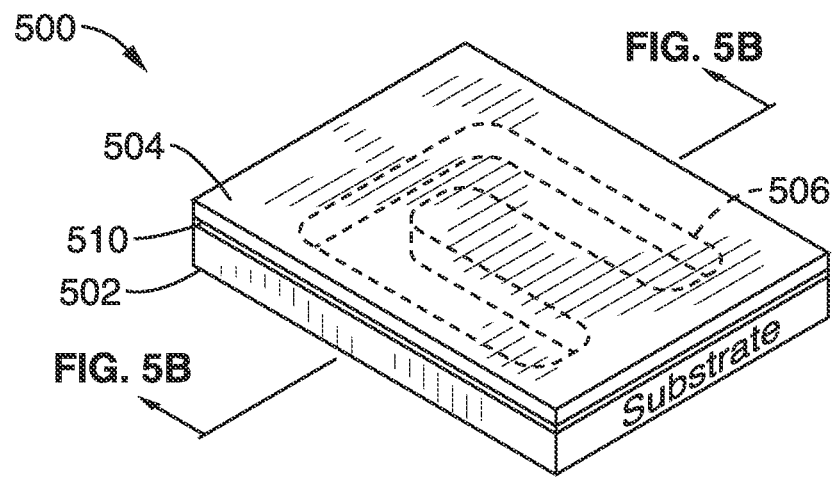
FIG. 5A is a perspective view of a bonded substrate assembly, where a flexible substrate has been bonded to a substrate cover.
Figure 5B:
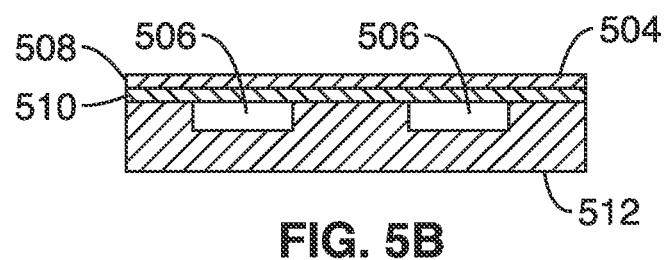
FIG. 5B is a cross section of the bonded substrate assembly of FIG. 5A.
Figure 5C:
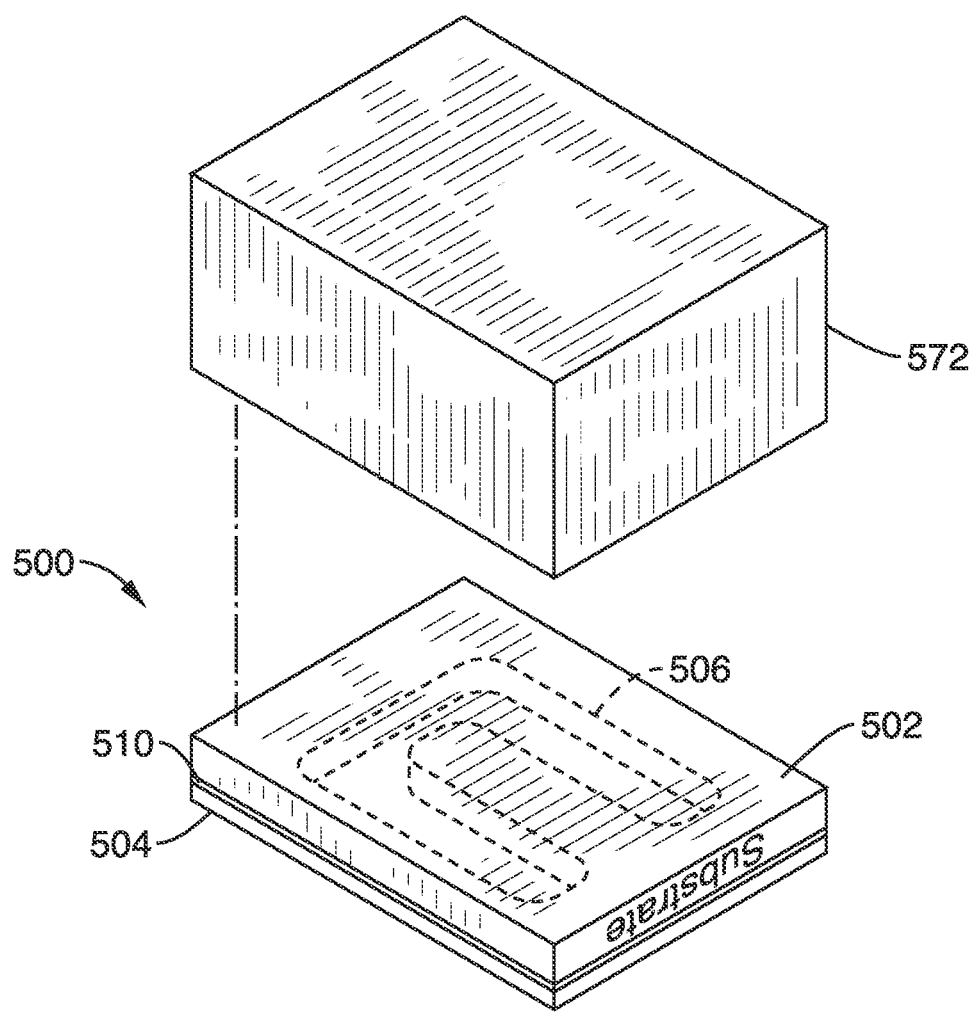
FIG. 5C is an exploded perspective view of a first method of bonding together the substrate assembly of FIG. 5A.

(2) In FIG. 5C the assembly is oriented upside down from FIG. 5A and FIG. 5B. Here, after curing the primer, a layer of flexible cement 510 (approximately 1 mm thick) is spread onto the attachment face 508 of the substrate cover 504. The substrate cover 504 is placed with the primed side facing up and the silicone flexible substrate 502 is placed on top of the flexible substrate 502. An evenly distributed light weight 572 (approximately 100 grams) is placed on top of the flexible substrate 502 to evenly distribute the flexible cement 510 over the area to be glued. Applying too much weight has been determined to significantly reduce the adhesion of the flexible cement 510.

Any imperfections in the adhesion between the substrate cover 504 and the flexible substrate 502 may produce gaps that will directly lead to water leakage from the closed channels 506.

8.2 Method 2

Figure 5D:
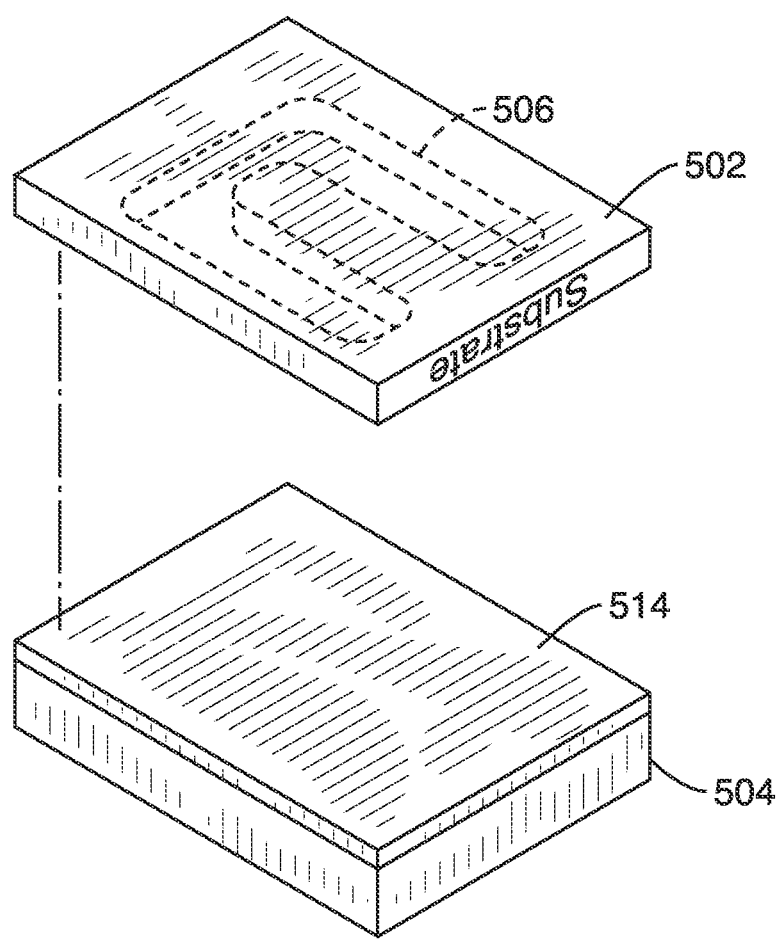
FIG. 5D is an exploded perspective view of a second method of bonding together the substrate assembly of FIG. 5A.

Refer now to FIG. 5D, where the second substrate assembly 500 bonding method comprises adding a layer of thermally conductive silicone 514 to the substrate cover 504, then gluing to the flexible substrate 502.

(1) This process is very similar to the previous one but with an added step.

(2) Primer is added to the substrate cover 504 as in Method 1.

(3) A thermally conductive silicone mixture is mixed together and degassed. In one non-limiting present embodiment, 50% silicone A (Insulcast 3-95-2) and 50% silicone B (Dow Corning Toray SE 4430) is prepared separately and used as the thermally conductive silicone mixture.

(4) Once prepared, the thermally conductive silicone mixture 512 is spread over the substrate cover 504, creating a layer as thin as possible while completely covering any exposed metal on the substrate cover 504. The substrate cover 504 and thermally conductive silicone mixture 512 is then set in the oven for 30 minutes at 120° C. When removed from the oven, any excess silicone is trimmed from the substrate cover 504 using a razor blade.

(5) The process from Method 1 above is then used for bonding the flexible substrate 502 onto the layer of thermally conductive silicone mixture 512.

8.3 Method 3

When using either Method 1 or Method 2, it is possible to reinforce the joint between substrate cover 504 and the flexible substrate 502 by applying stitches (either by hand or a professional sewing machine) through the substrate cover 504 and the flexible substrate 502 while the respective adhesive (flexible cement 510 in Method 1, and thermally conductive silicone mixture 512 in Method 2) is still not fully cured.

9. Functional Performance of a Flat Heat Exchanger Module

Figure 6A:
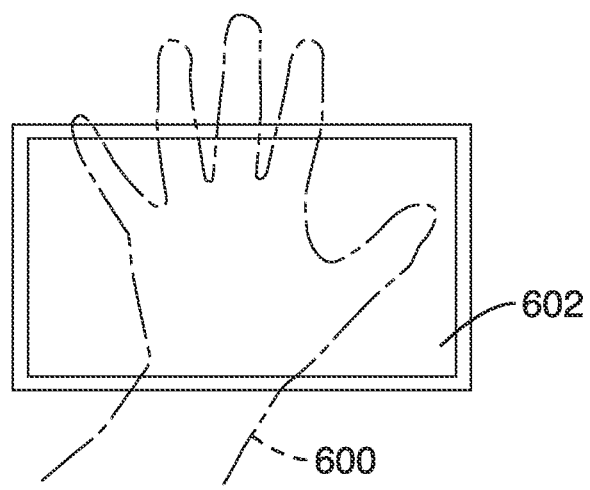
FIG. 6A is a top view of a human hand touching a flat heat exchanger module.

FIG. 6A shows a test setup of a volunteer's hand 600 disposed upon a heat exchanger module 602 comprised of a rectangular array of 16-15 mm×15 mm TECs (not shown) arranged in a 4×4 grid pattern.

Figure 6B:
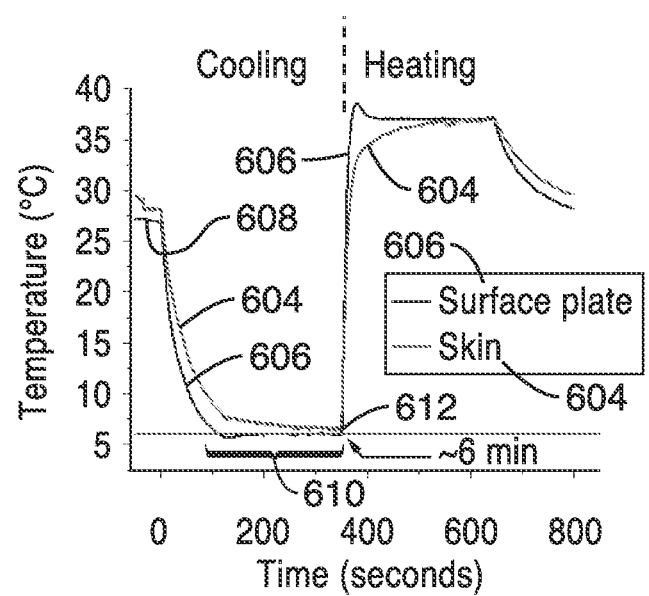
FIG. 6B is a graph of temperature versus time measured on the skin 604 of the hand of an individual in response to cooling (to 5° C.) and heating (to 36° C.) using controlled profiles of the heat exchanger module.

FIG. 6B shows a graph of the skin temperature 604 of the volunteer's hand 600 upon cooling and heating of the HEM 602 upon direct contact. Note that a stable controlled temperature is attained in less than 360 seconds after turning on HEM 602 in cooling mode. Heating of the HEM 602 occurred much more quickly, with about a 30° C. plate and skin temperature rise over the course of about 20 s. This graph also contains data for the surface plate 606 temperature change versus time, showing close agreement between the hand skin 604 and the surface plate 606 temperatures.

It should be noted that there is an "onset point" for cooling 608 (leftmost point of inflexion) evidencing by applying the power to the HEM. As an example, the surface plate temperature change occurs in ~5 sec, and the skin temperature change is slower but complete within 6 min.

There is a period of stable cold temperature HEM control 610 (for example, 7° C. in FIG. 6B) that can last for as long as needed (6 min in FIG. 6B). The temperature transitions are programmable and can be adjusted to be slower than those shown in FIG. 6B.

There can be an "onset point" 612 for heating. This is shown as an example at the 6 min mark 612 in FIG. 6B. The heating temperature can be controlled at any value (e.g. 37° C. in FIG. 6B) for as long as needed.

The actual temperatures and durations of the heating and cooling episodes are software-controlled and can be applied in repeatable patterns as requested by medical professionals. Existing technology (going from ice [or cold water] to a hot water application) is not capable of achieving either fast temperature transitions or patterned cooling and heating episodes.

The temperature controlled patterns in FIG. 6A and FIG. 6B can be attained in any tissue, not just the hands (by using a flat HEM) and the thighs (by using a curved HEM).

10. Curved Heat Exchanger Modules

One feature of this HEM technology is the possibility to create ergonomic curved HEMs that are specifically designed to follow the contours of body parts. The resulting HEM may be curved, flat, or tailor-made to cover large surfaces of various body parts. The procedures described above to create flat HEMs need to be modified for making HEMs with curvature. The differences for each section of the cooler are described below.

The biggest difference with curved HEMs comes in casting the molds for the channels. The flat acrylic molds must be replaced by specifically designed molds cast through the following process:

(1) Initially, a negative of the mold is designed in SolidWorks or other 3D computer aided design (CAD) software package.

Figure 7A:
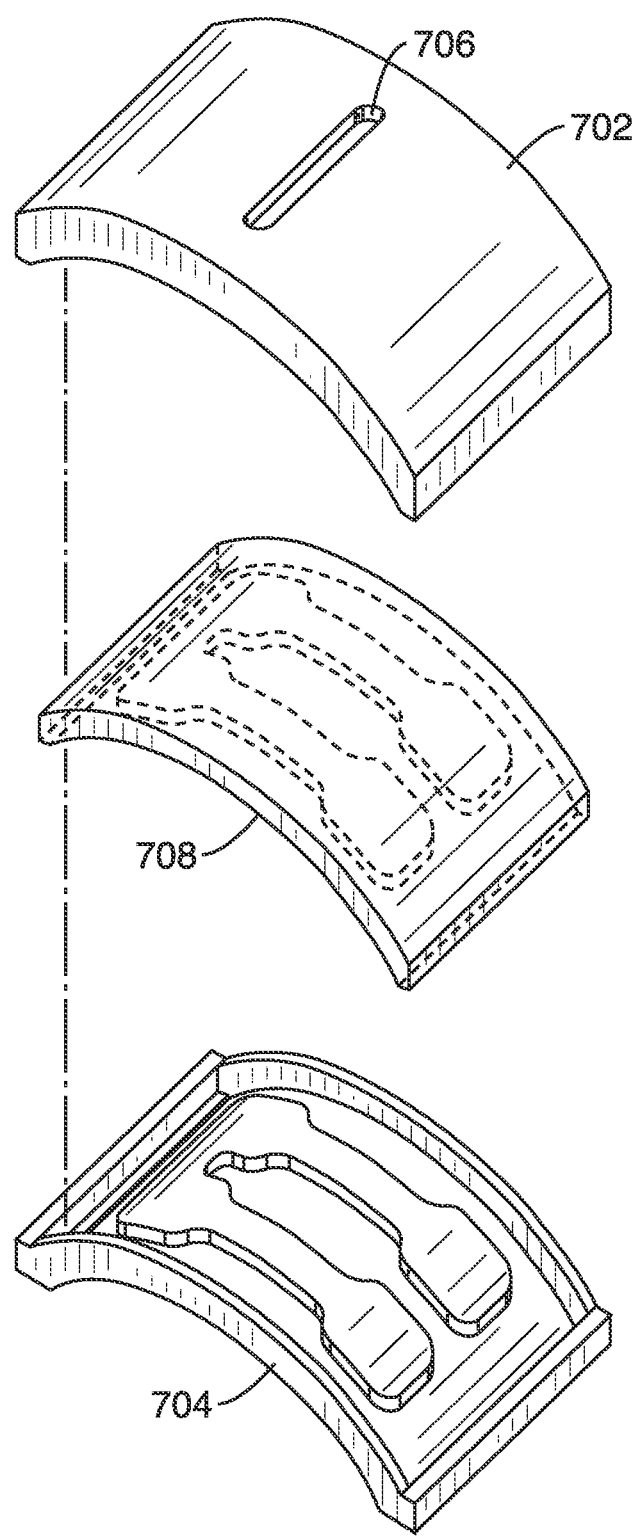
FIG. 7A is an exploded perspective view of an upper and lower mold, forming a flexible substrate.

Refer now to FIG. 7A, which shows an exploded embodiment of a curved HEM flexible substrate mold 700 set. The mold 700 set design is then sent to a 3D printer in two sections, a top 702 and a bottom 704. The top 702 and bottom 704 of the mold 700 are joined together and ready to produce a molded part 708.

(2) The silicone (or other casting plastic) is then prepared as usual and then poured into the bottom 704 section of the mold 700. Any reinforcement mesh would be added before placing the top 702 mold above the bottom 704. The rest of silicone would be poured into the mold set 700 through holes 706 in the top 702 until it overflows.

(3) The silicone is left to set for two hours and then the mold 700 top 702 and bottom 704 are removed from around the flexible substrate 708.

(4) An identical process is envisioned for design and assembly of medium/large scale production of HEMs using injection molding procedures.

Figure 7B:
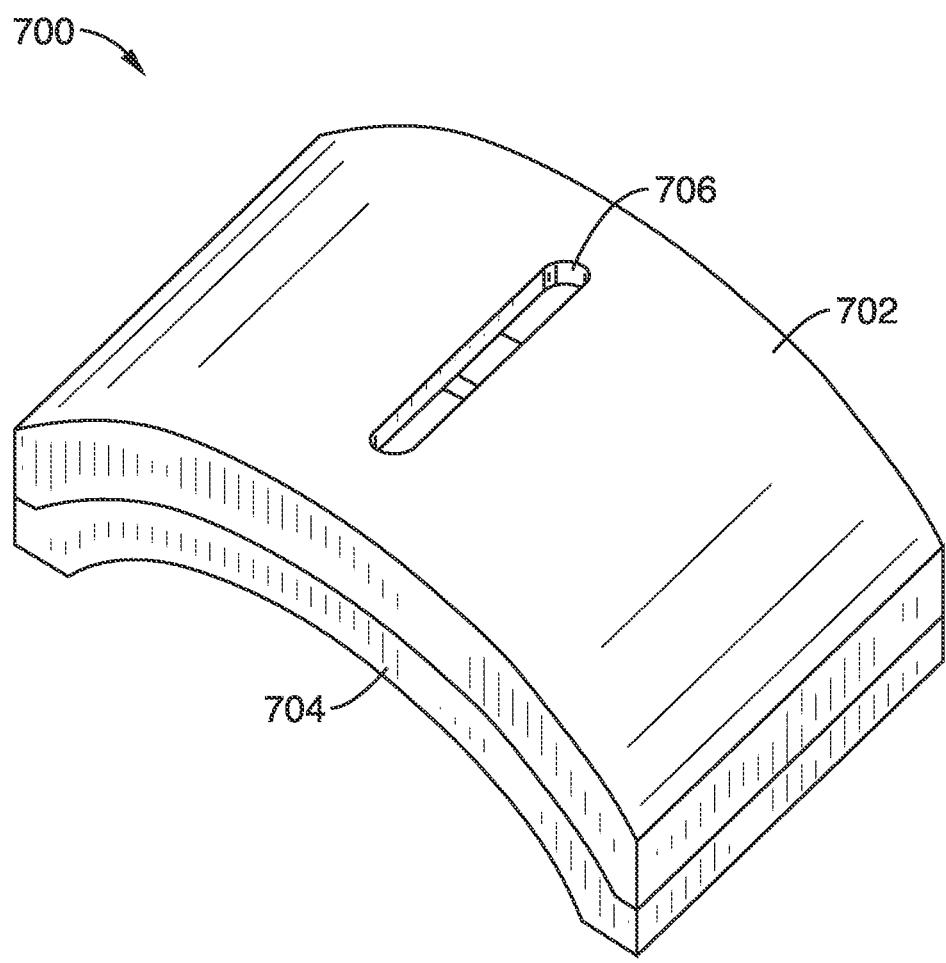
FIG. 7B is an assembled perspective view of the assembled upper and lower mold of FIG. 7A.

Refer now to FIG. 7B, where the mold 700 set has been assembled and is ready for molding.

11. Curved Substrate Covers and Interface Covers

The making of the two covers is not substantially different in the curved geometry from the flat geometry. The only modification comes after the plates are cut, since bending of the covers with a roller would be necessary until the covers fit the curvature of the curved flexible substrate.

The thermistor would be applied to the interface cover after it has been bent to the curved shape to prevent it from being dislodged during the bending process.

Figure 8A:
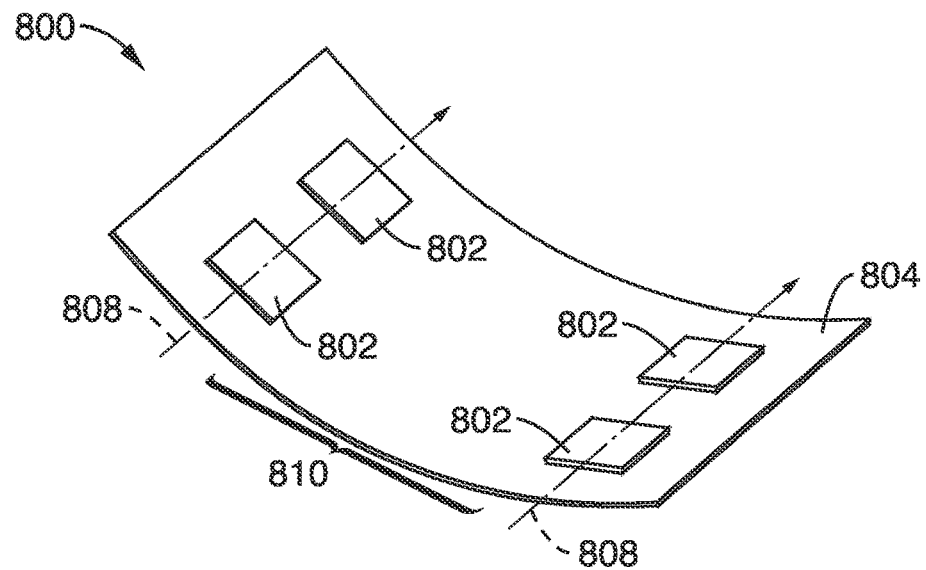
FIG. 8A is a perspective view of a substrate cover assembly.
Figure 8B:
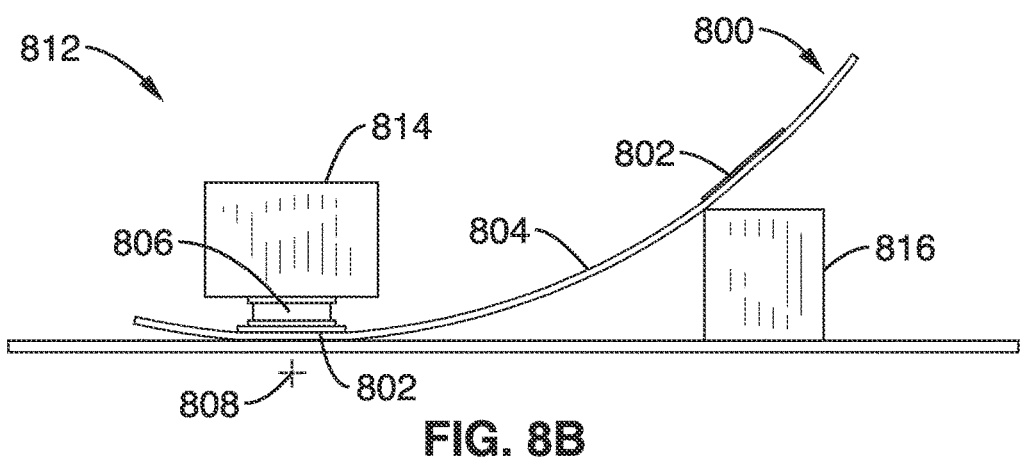
FIG. 8B is a side view of the process of setting a first row of thermoelectric coolers (TECs) onto the substrate cover of FIG. 8A.
Figure 8C:
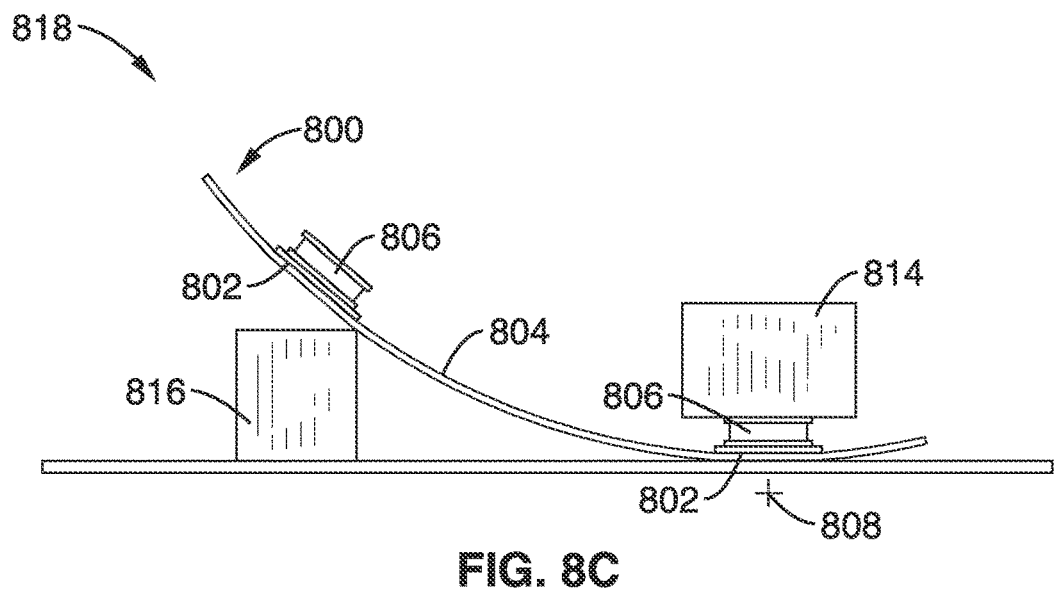
FIG. 8C is a side view of the process of setting a second row of thermoelectric coolers (TECs) onto the substrate cover of FIG. 8A.

Refer now to FIG. 8A through FIG. 8C. FIG. 8A is a perspective view of a substrate cover assembly 800 that has had copper squares 802 bonded to the substrate cover 804. Future TECs (806 of FIG. 8B and FIG. 8C) will be mounted to the copper squares 802. One aspect of this process is that the copper squares 802 act as reinforcing stiffeners to the substrate cover 804 where they are attached. This means that the substrate cover 804 will tend to remain relatively flatter in areas below the copper squares 802.

It should be noted that the copper squares 802 are disposed in rows 808 parallel to the axis of curvature (not shown). The copper squares 802 are spaced apart 810 to allow for the curvature of the substrate cover 804 to be formed.

Refer now to FIG. 8B and FIG. 8C. FIG. 8B is a side view 812 of the substrate assembly 800 in the process of having a row of TECs 806 bonded to the substrate cover 804 on the copper squares 802 along the first row 808. A weight 814 is temporarily applied to one or more of the TECs 806 to promote adhesion between the TECs 806 and the substrate cover 804. The weight 814 is removed after the bonding of the first row 808 of the TECs 806. A removable support 816 may be provided to prevent unintentional bending of the substrate assembly 800

Similarly, in FIG. 8C, a second row of TECs 806 is being bonded 818 to the substrate cover 804 with the assistance of temporary weight 814 on the TECs 806 in the second row 808 of attachment.

It should be noted that the process for arranging the TECs 806 is slightly altered for the curved substrate assemblies 800. To allow for greater flexibility along the direction of curvature, the TECs 806 are designed to be farther spaced apart 810 in the direction of curvature. The TECs 806 are generally designed to be in lines 808 perpendicular to the direction of curvature, or parallel to the axis of curvature.

The various rows 808 of TECs 806 allow for easier adhesion of the TECs 806 to the copper squares 802, as gluing is most easily done in sections. This is due to the curvature of the substrate cover 804 and the need to apply pressure to the TECs 806 for proper adhesion.

12. Curved Substrate Cover to Curved Flexible Substrate Bonding

Figure 9A:
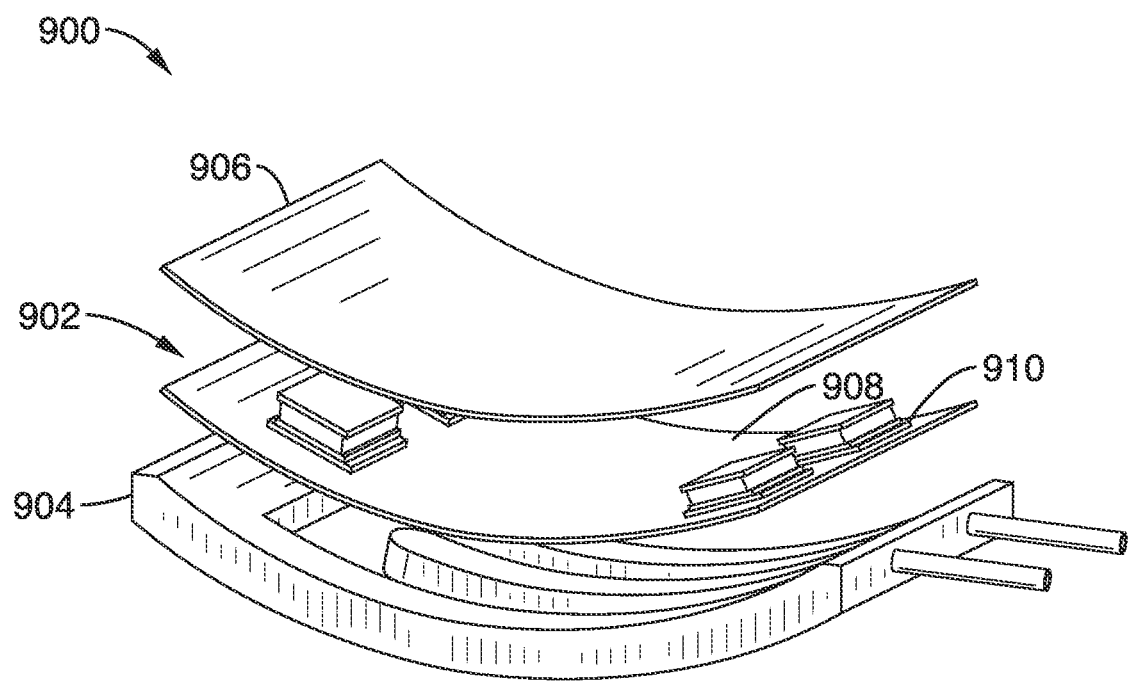
FIG. 9A is an exploded perspective view of the principal components of a curved heat exchanger module (HEM).
Figure 9B:
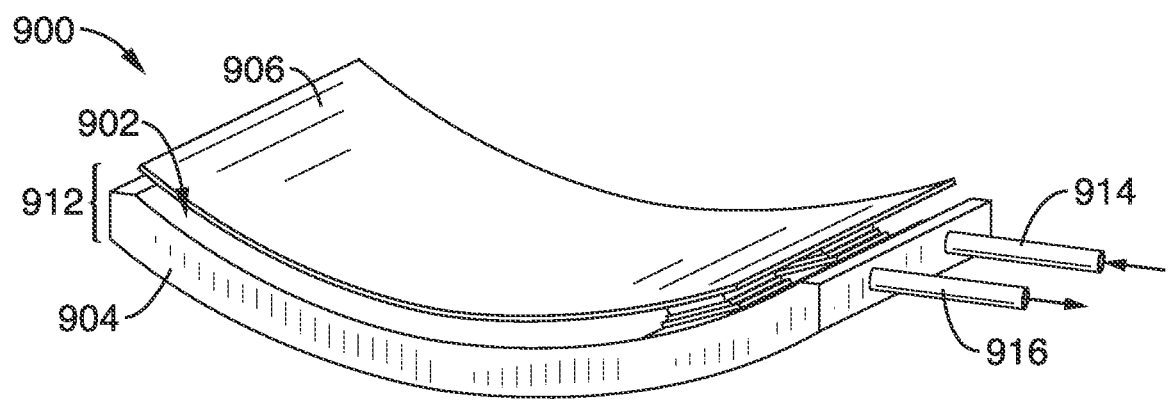
FIG. 9B is a perspective view of the assembled principal components the curved heat exchanger module (HEM) of FIG. 9A.

Refer now to FIG. 9A and FIG. 9B. In FIG. 9A, an exploded view of the principal components of a curved heat exchanger module 900 is shown. The curvatures of the substrate cover assembly 902, the flexible substrate 904, and the interface cover 906 makes even tougher the already difficult task of adhering the various surfaces together.

FIG. 9B shows the assembled curved heat exchanger module 900 from the exploded view of FIG. 9A.

As stated previously, since the substrate cover 908 slightly bends around the copper squares 910, it only approximates the curvature of the channels. This may cause small gaps between the substrate cover 908 and the flexible substrate 904 where the adhesive (not shown here) is applied.

In order to prevent such adhesive gaps in the gluing process, pressure must be applied to both sides. However, as stated earlier, too much pressure may diminish the quality of the gluing between the surfaces. Thus, there is a fine tuning between too much or too little pressure for this process and care must be taken to carry it out correctly.

In an alternative embodiment, the substrate cover assembly 902 is bonded to the flexible substrate 904 by molding the substrate cover assembly 902 into the combined 912 flexible substrate 904 and substrate cover assembly 902. Here, the substrate cover assembly 902 is bent beforehand, and then placed into a mold. Liquid silicone is then poured into the mold, forming the flexible substrate 902 in place, already bonded to the substrate cover assembly 902. This process eliminates the gaps caused by the copper squares 910, and as a result makes the second method much more suitable for the curved HEMs.

For the interface cover and insulation of the interstitial gap (neither shown here), the fabrication processes remain unchanged between curved and flat HEMs.

Similarly to the flat version of the HEM of FIG. 3A, there are liquid input 914 and liquid outlet 916 tubes to flow a heat transfer medium through the HEM 900.

13. Articulated Heat Exchanger Module (HEM) Assemblies of Multiple HEM Components Another embodiment of the HEM technology is the assembly of multiple HEM cooling or heating units together to conform to complex geometries that retain the individual properties of individual HEMs but that can perform larger scale functions.

Figure 10A:
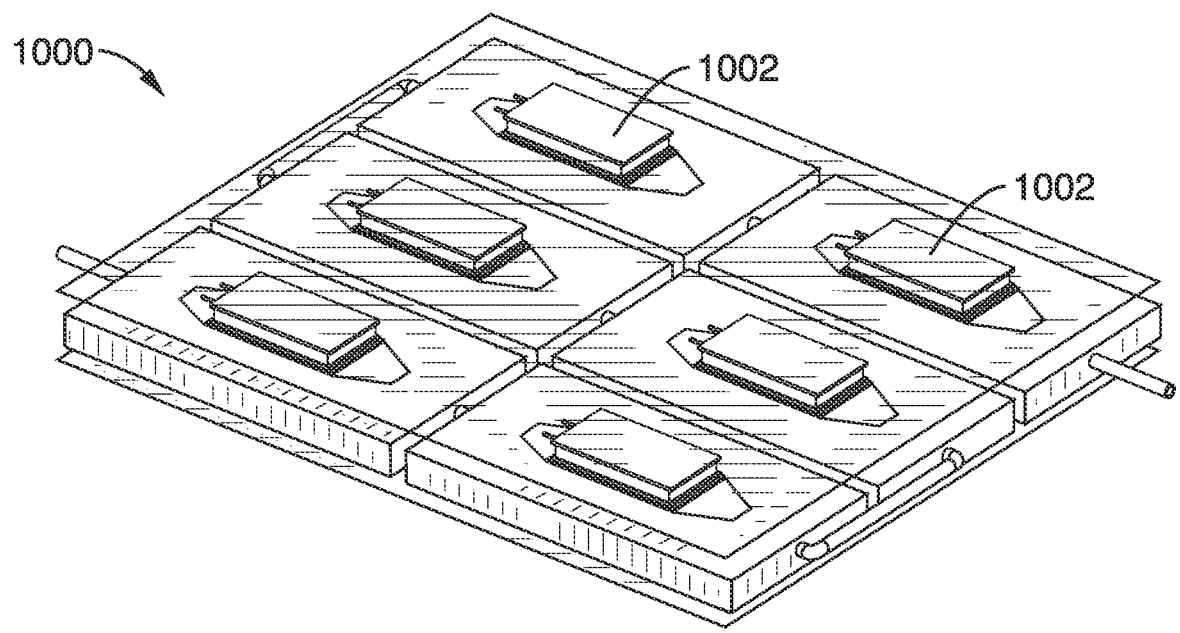
FIG. 10A is a perspective view of 6 single thermoelectric cooler (TEC) heat exchanger modules combined to for a single articulated flat HEM assembly.
Figure 10B:
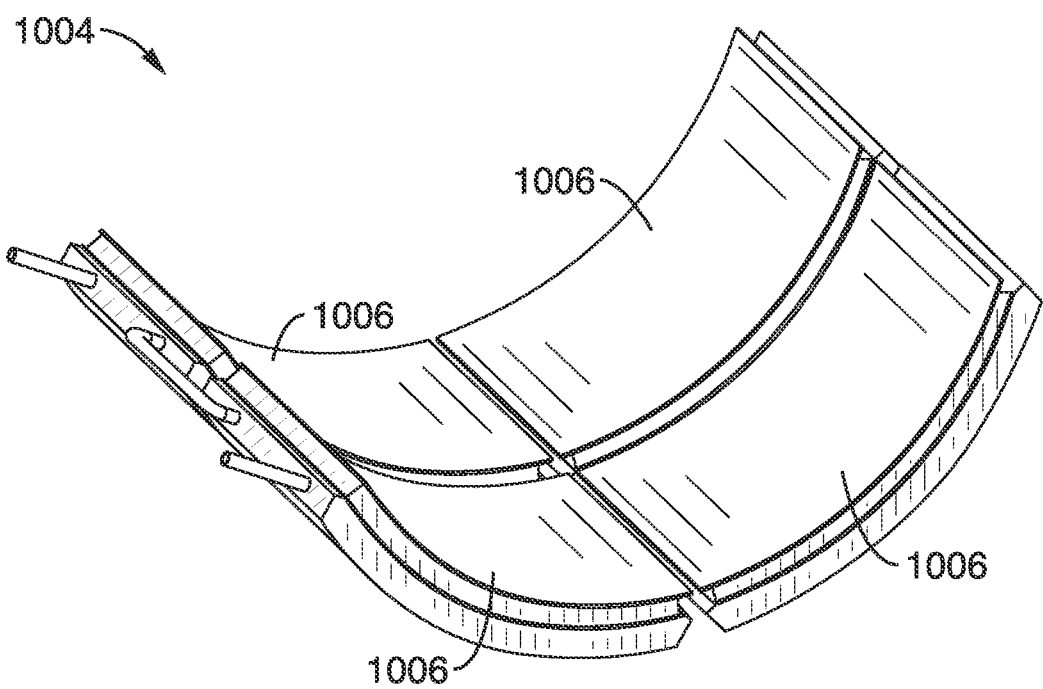
FIG. 10B is a perspective view of 4 single TEC HEMs assembled into a single curved HEM articulated assembly.

Refer now to FIG. 10A and FIG. 10B. FIG. 10A shows an assembled view of a flat HEM 1000 of 6 TECs 1002 each comprising a single 20×40 mm TEC.

FIG. 10B shows an assembled view 1004 of a set of 4 assembled curved HEMs 1006 suitable for cooling or heating the brachialis or brachioradialis muscles of a human arm, where each HEM is based on 4-15×15 mm TECs. The HEMs in the assemblies are connected by flexible tubing for fluid circulation, and the TECs are connected electrically to operate in serial or parallel banks. An advantage of the multiple assembly of HEMs is the extra flexibility and articulation ability that is afforded by gaps between the individual HEMs while connected by flexible tubing. These gaps may be filled with a compliant foam to create a fully articulated soft heat exchanging unit. Thermistors in each HEM are used to provide feedback into the ESU in such a way that the average temperature throughout the assembly can be controlled or maintained within predefined ranges.

14. The Functional Performance of a Curved Heat Exchanger Module (HEM)

Figure 11A:
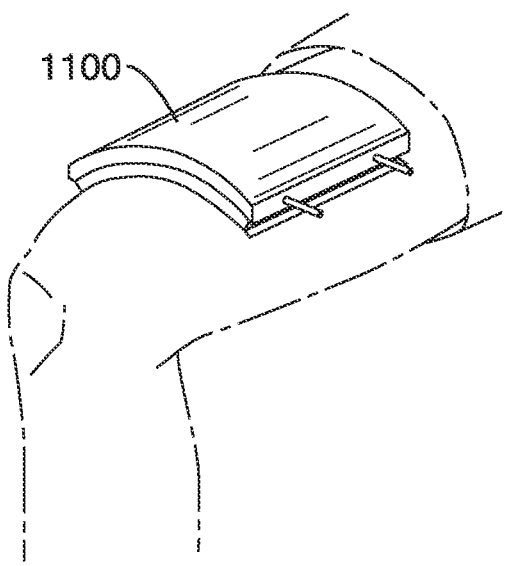
FIG. 11A is a perspective view of a curved ergonomic HEM of 15 mm×15 mm TECs applied to a volunteer's thigh.
Figure 11B:
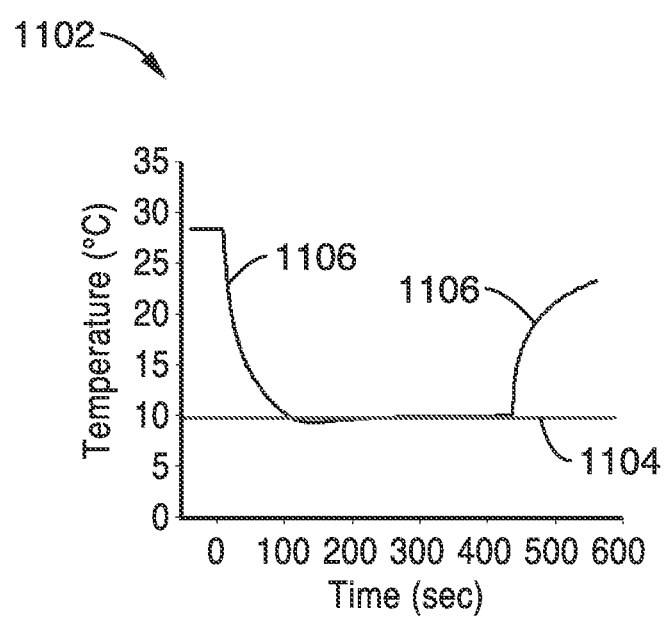
FIG. 11B is a graph of temperature changes measured on the thigh (rectus femoris muscle) of an individual in response to controlled cooling to 10° C. for approximately 7 min.

Refer now to FIG. 11A and FIG. 11B. FIG. 11A is a perspective view of a curved ergonomic HEM 1100 of 15 mm×15 mm TECs applied to a volunteer's thigh.

FIG. 11B shows a temperature versus time plot 1102 of the volunteer's thigh cooling when in contact with a curved ergonomic HEM 1100 made with an array of eight 15×15 mm TECs of FIG. 11A. Straight line 1104 indicates the temperature of the curved ergonomic HEM 1100 of FIG. 11A. Curve 1106 indicates that a stable controlled skin temperature is attained in less than 300 s after turning on the HEM 1100 cooling process.

15. Examples of HEMs for Specific Medical Applications

15.1 Head and Neck Cooling

The HEM technology can be adapted for local cooling of the head and neck aiming to reduce and modulate the temperature of the cerebral cortex (i.e., the outer part of the brain). This therapy modality is promising for treatment of acute brain injuries, for instance: trauma, stroke, hypoxic-ischemic encephalopathy after cardiac arrest, encephalopathy, and seizures. Also, it can be used as adjunct therapy in preparation for brain procedures (i.e. surgery and endovascular procedures), where protection of the brain tissue is relevant. This device can also be used for the treatment of headache, as cooling has analgesic (pain-killing) effects.

15.2 Neonatal Uses

Figure 12A:
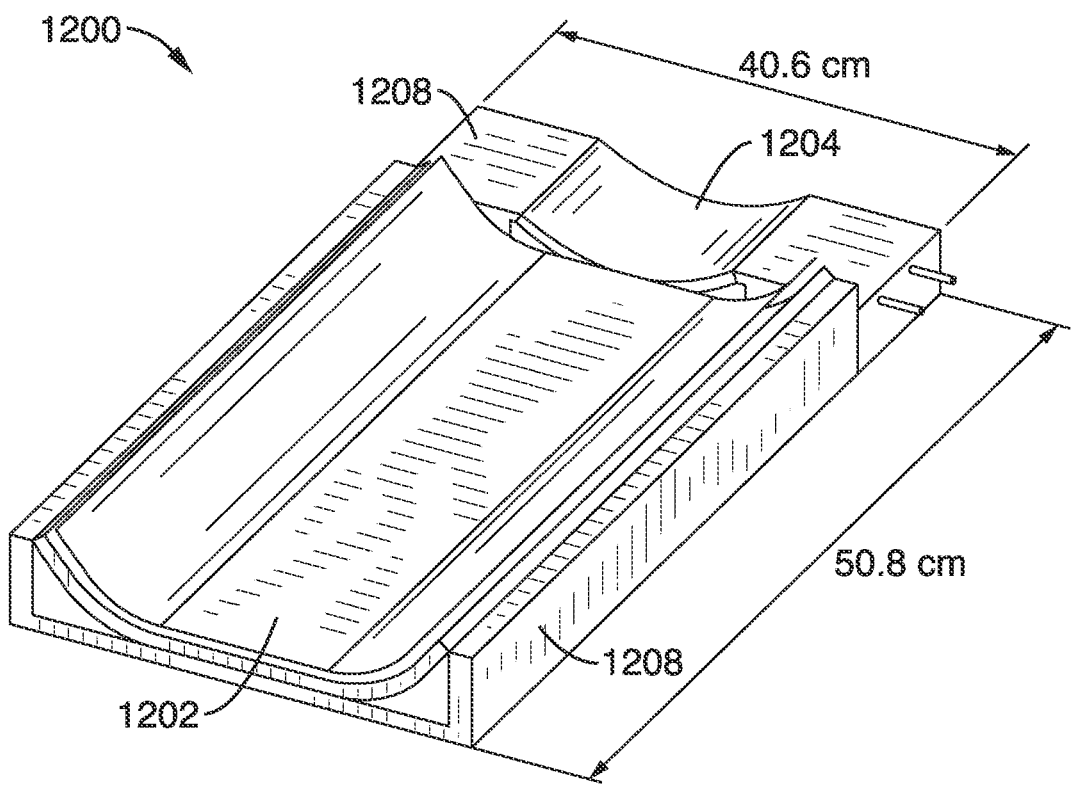
FIG. 12A is a perspective view of an assembly of HEMs in various geometries intended for use with neonates.
Figure 12B:
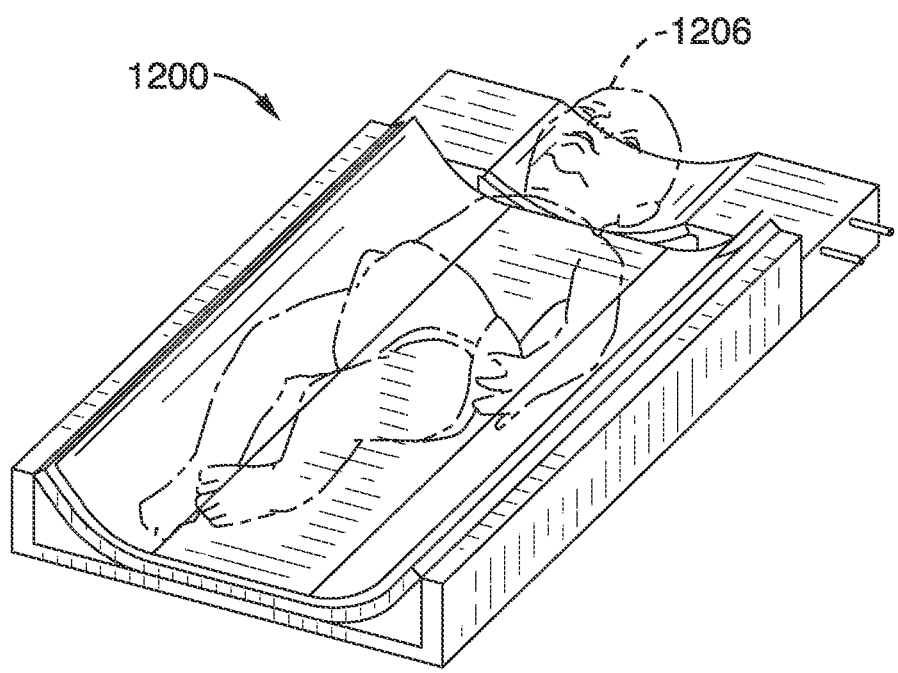
FIG. 12B is a perspective view of a neonate placed upon the assembly of HEMs of FIG. 12A.

Refer now to FIG. 12A through FIG. 12C. Here, an HEM assembly 1200 may comprise mattress 1202 and cradle 1204 configurations of HEMs. Such an assembly 1200 may be used for the hypothermia treatment of neonatal Hypoxy Ischemic Encephalopathy (HIE). HEM technology can be employed to moderate the whole body temperature of newborn babies 1206 with hypoxic-ischemic encephalopathy (also called neonatal asphyxia).

Foam insulation 1208 may be used in conjunction with the HEM mattress 1202 and cradle 1204 configurations to decrease cooling load required by the HEM components.

Such an HEM assembly 1200 may induce cooling, modulate the baby's 1206 body temperature, and re-warm the baby 1206 gradually. This device would be fully portable and battery operated, being ideal for transport between facilities or inside a facility, a distinction not shared by currently available neonatal heating and cooling units.

15.3 Cooling Pads for Muscle Injuries

HEM technology can be applied for treatment of acute muscular-skeletal injuries, inducing and maintaining cooling of the affected tissue. Unlike currently used devices, HEM technology is highly efficient at maintaining surface temperature with very little variation. The devices are ergonomically designed to conform to various body parts, such as ankles, wrists, elbows, knees, back, and neck.

15.4 Thermo-Controlled Surface HEM for Operating Tables

Figure 13:
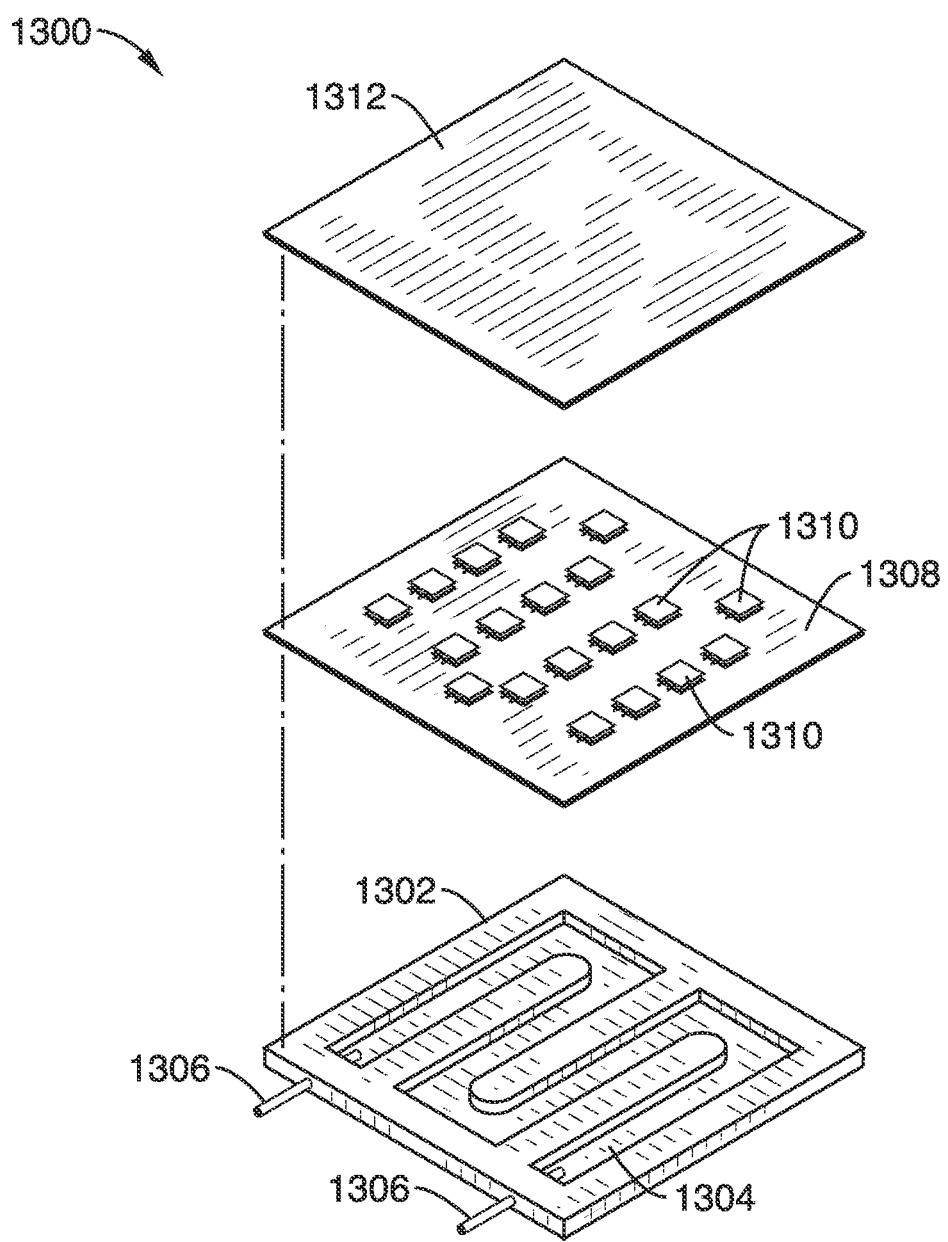
FIG. 13 is a perspective exploded view of the major components of an HEM in a flat mattress or blanket configuration.

Refer now to FIG. 13, which is an exploded perspective view of a blanket or mattress pad 1300 employing HEM technology. The blanket or mattress pad 1300 may be used to maintain the body temperature of patients receiving a surgical procedure, with body temperatures being monitored and controlled by the operator. This device can warm or cool as desired by the operator. It can rapidly induce temperature changes as needed for a particular procedure. In this FIG. 13, only the basic HEM elements of flexible substrate 1302 molded channels 1304, input and output ports 1306, substrate cover 1308, TECs 1310, and interface cover 1312 are shown, as these have all been described above in more detail.

15.5 Thermoregulatory Post-Surgical Rehabilitation Device

HEM technology could be deployed in the post-operative care of limb surgery, including a cast-like immobilization apparatus that could be used to deliver hypothermia and immobilization for bone fractures, joint dislocation, or sprains. In addition, HEM technology could be used as adjuvant for pain management and containment of tissue trauma, during the rehabilitation period of surgical procedures involving muscles, bones, and joints.

From the description herein, it will be appreciated that that the present disclosure encompasses multiple embodiments which include, but are not limited to, the following:

1. A heat exchange system comprising: (a) a heat exchanger module, the heat exchanger module comprising: (i) a flexible substrate, the flexible substrate comprising one or more open channels; (ii) a substrate cover bonded over the flexible substrate; (iii) whereby the substrate cover when bonded over the open channels thereby forms closed channels to allow for circulation of a liquid; (iv) a plurality of thermoelectric coolers bonded to the substrate cover on a reference side of the thermoelectric coolers; and (v) an interface cover bonded to the thermoelectric coolers on an patient side opposite from the reference side; (b) one or more temperature sensors disposed within the heat exchanger module, wherein the temperature sensors sense a temperature of the interface cover; and (c) a controller configured to use the temperature sensors to control the interface cover temperature by varying a supply current to the thermoelectric coolers; (d) wherein the temperature of the interface cover is controlled by the controller.

2. The system of any preceding embodiment, wherein the heat exchanger module is selected from a group of geometries consisting of: substantially flat, curved in one direction, and curved in more than one direction.

3. The system of any preceding embodiment, wherein the heat exchanger module system is battery powered.

4. The system of any preceding embodiment, wherein the liquid comprises water.

5. The system of any preceding embodiment, wherein the temperature sensors are selected from a group of sensors consisting of: a thermistor, a thermocouple, and a solid state device that outputs a voltage or current proportional to temperature.

6. The system of any preceding embodiment, wherein the controller uses a control algorithm selected from one or more algorithms consisting of: proportional, integral, and derivative.

7. The system of any preceding embodiment, wherein the controller is digital, with zero or more analog components.

8. The system of any preceding embodiment, wherein the supply current is supplied by a current supply selected from a group of current supplies consisting of: a class D amplifier, an H-bridge amplifier, and a pulse width modulated source.

9. The system of any preceding embodiment, wherein the heat exchanger module either heats or cools the interface cover.

10. A heat exchanger system comprising: (a) a heat exchanger module, the heat exchanger module comprising: (i) a plurality of thermoelectric coolers; (ii) a flexible substrate supporting the thermoelectric coolers, the substrate having a plurality of channels configured for circulating a liquid in thermal proximity to the thermoelectric coolers; and (iii) one or more temperature sensors disposed in proximity to the flexible substrate; and (b) a controller configured to use the temperature sensors to monitor a temperature of an object adjacent to the heat exchanger module, and configured to control circulation of the liquid; (c) wherein the temperature of an object in contact with the heat exchanger module can be changed by heat transfer between the thermoelectric coolers and the liquid, and wherein the amount of temperature change can be controlled by the controller.

11. The system of any preceding embodiment, wherein the heat exchanger module is flat.

12. The system of any preceding embodiment, wherein the heat exchanger module is curved.

13. A heat exchanger module comprising: (a) a flexible substrate, the flexible substrate comprising one or more open channels; (b) a substrate cover bonded over the flexible substrate; (c) whereby the substrate cover when bonded over the open channels thereby forms closed channels to allow for circulation of a liquid; (d) a plurality of thermoelectric coolers bonded to the substrate cover on a reference side of the thermoelectric coolers; (e) an interface cover bonded to the thermoelectric coolers on an patient side opposite from the reference side; and (f) one or more temperature sensors disposed within the heat exchanger module.

14. The heat exchanger module of any preceding embodiment, wherein the temperature sensors sense a temperature of the interface cover.

15. The heat exchanger module of any preceding embodiment, wherein the heat exchanger module is substantially flat.

16. The heat exchanger module of any preceding embodiment, wherein the heat exchanger module is curved in one or more directions.

17. The heat exchanger module of any preceding embodiment, wherein the liquid comprises water.

18. The heat exchanger module of any preceding embodiment, wherein the temperature sensors are selected from a group of sensors consisting of: a thermistor, a thermocouple, and a solid state device that outputs a voltage or current proportional to temperature.

19. The heat exchanger module of any preceding embodiment, wherein the heat exchanger module either heats or cools the interface cover.

20. The heat exchanger module of any preceding embodiment, wherein a rate of heating or cooling the interface cover is controlled.

21. A method of using a heat exchanger module, comprising: (a) applying a heat exchanger module to a patient, the heat exchanger module comprising: (i) a flexible substrate, the flexible substrate comprising one or more open channels; (ii) a substrate cover bonded over the flexible substrate; (iii) whereby the substrate cover when bonded over the open channels thereby forms closed channels to allow for circulation of a liquid; (iv) a plurality of thermoelectric coolers bonded to the substrate cover on a reference side of the thermoelectric coolers; (v) an interface cover bonded to the thermoelectric coolers on an patient side opposite from the reference side; and (vi) one or more temperature sensors disposed within the heat exchanger module; and (b) applying a thermal treatment to the patient by using the heat exchanger module.

22. The method of using the heat exchanger module of any preceding embodiment, wherein the thermal treatment uses a controlled rate of heating.

23. The method of using the heat exchanger module of any preceding embodiment, wherein the thermal treatment uses a controlled rate of cooling.

24. The method of using the heat exchanger module of any preceding embodiment, wherein the thermal treatment uses a time period of substantially constant heat exchanger module interface cover temperature.

25. A neonatal heat treatment device comprising: (a) one or more flat heat exchanger modules; and (b) one or more curved heat exchanger modules; (c) each said heat exchanger module comprising: (i) a flexible substrate, the flexible substrate comprising one or more open channels; (ii) a substrate cover bonded over the flexible substrate; (iii) whereby the substrate cover when bonded over the open channels thereby forms closed channels to allow for circulation of a liquid; (iv) a plurality of thermoelectric coolers bonded to the substrate cover on a reference side of the thermoelectric coolers; (v) an interface cover bonded to the thermoelectric coolers on an patient side opposite from the reference side; and (vi) one or more temperature sensors disposed within the heat exchanger module.

26. A method of assembling a heat exchanger module, comprising: (a) providing a flexible substrate, comprising one or more open channels; (b) providing a substrate cover; (c) providing an interface cover; (d) bonding a plurality of thermoelectric coolers to the substrate cover on a reference side of the thermoelectric coolers; (e) attaching one or more temperature sensors to the interface cover; and (f) bonding the interface cover to the thermoelectric coolers on an patient side opposite from the reference side; (g) whereby the substrate cover bonded over the open channels thereby forms closed channels to allow for circulation of a liquid.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A heat exchange system comprising:
   (a) a heat exchanger module the heat exchanger module comprising:
      (i) a flexible substrate, the flexible substrate comprising one or more open channels having a fluid input and fluid output;
      (ii) a substrate cover, selected from a group of materials consisting of copper, aluminum, brass, stainless steel, carbon fiber composites and pyrolytic graphite, bonded over the flexible substrate;
      (iii) whereby the substrate cover when bonded over the open channels thereby forms closed channels to allow for circulation of a liquid in and out of the channels through said fluid input and fluid output;

(iv) a plurality of thermoelectric coolers bonded to the substrate cover on a reference side of the thermoelectric coolers;
(v) an interface cover bonded with a thermally conductive adhesive to the thermoelectric coolers on a patient side opposite from the reference side;
(vi) a biocompatible elastomeric layer disposed on said interface cover to provide substantially uniform cooling or heating on body tissues to which the heat exchanger module is applied; and
(vii) a thermal insulation material, preformed with interstitial gaps and device gaps allowing placement of the preformed thermal insulation material over and around the thermoelectric coolers, between said substrate cover and said interface cover, said thermal insulation configured to provide structural support and minimize heat transfer between the substrate cover and said interface cover which would diminish heat transfer efficiency;
(b) one or more temperature sensors disposed within the heat exchanger module attached within one of the interstitial gaps, prior to placement of the preformed thermal insulation material over and around said thermoelectric coolers, to monitor temperature within the interstitial gap, wherein the temperature sensors sense a temperature of the interface cover;
(c) a heat exchanger and pump providing circulation of the liquid in a closed-loop between the radiator and a water reservoir of said heat exchanger and hoses directing the liquid to each fluid inlet and fluid outlet of each closed channel in the heat exchanger module, and with a fan configured for forcing air through said heat exchanger;
(d) a controller comprising a servocontrol unit having a proportional-integral-derivative (PID) and a pulse width modulator (PWM) configured for varying a supply current to the thermoelectric coolers through a high current H-bridge to control the interface cover temperature based on measurements from said temperature sensors;
(e) an operator interface coupled to said controller; and
(f) wherein the temperature of the interface cover is controlled by the controller through said operator interface for reading and setting temperatures, starting and stopping cooling and heating profiles, defining upper and lower limits for cooling and heating ranges, accessing routines for optimizing PID parameters, accessing routines to program fluid and heat exchange rates, selecting between AC or battery operation, graphically displaying temperature plots, and providing an emergency button which can be accessed to halt the cooling or heating operation of the heat exchange system.

2. The system of claim 1, wherein the heat exchanger module is selected from a group of geometries consisting of: substantially flat, curved in one direction, and curved in more than one direction.

3. The system of claim 1, wherein the heat exchanger module system is battery powered.

4. The system of claim 1, wherein the liquid comprises water.

5. The system of claim 1, wherein the temperature sensors are selected from a group of sensors consisting of: a thermistor, a thermocouple, and a solid state device that outputs a voltage or current proportional to temperature.

6. The system of claim 1, wherein the controller uses a control algorithm selected from one or more algorithms consisting of: proportional, integral, and derivative.

7. The system of claim 1, wherein the controller is digital, with zero or more analog components.

8. The system of claim 1, wherein the heat exchanger module either heats or cools the interface cover.

9. A heat exchanger module comprising:
(a) a flexible substrate, the flexible substrate comprising one or more open channels having a fluid input and fluid output configured for coupling to a heat exchanger;
(b) a substrate cover, selected from a group of materials consisting of copper, aluminum, brass, stainless steel, carbon fiber composites and pyrolytic graphite, bonded over the flexible substrate;
(c) whereby the substrate cover when bonded over the open channels thereby forms closed channels to allow for circulation of a liquid in and out of the channels through said fluid input and fluid output;
(d) a plurality of thermoelectric coolers bonded to the substrate cover on a reference side of the thermoelectric coolers;
(e) an interface cover bonded with a thermally conductive adhesive to the thermoelectric coolers on a patient side opposite from the reference side;
(f) a biocompatible elastomeric layer disposed on said interface cover to provide substantially uniform cooling or heating on body tissues to which the heat exchanger module is applied;
(g) a thermal insulation material, formed with interstitial gaps and device gaps allowing placement of the preformed thermal insulation material over and around the thermoelectric coolers, between said substrate cover and said interface cover, said thermal insulation configured to provide structural support and minimize heat transfer between the substrate cover and said interface cover which would diminish heat transfer efficiency;
(h) one or more temperature sensors disposed within the heat exchanger module attached within one of the interstitial gaps, prior to placement of the preformed thermal insulation material over and around said thermoelectric coolers, to monitor temperature within the interstitial gap, wherein the temperature sensors sense a temperature of the interface cover; and
(i) copper squares mounted on said interface cover and/or said substrate cover at locations where each of said plurality of thermoelectric coolers are to be bonded, toward preventing a respective cover from bending around the thermoelectric coolers and for providing enhanced thermal diffusion.

10. The heat exchanger module of claim 9, wherein the temperature sensors are attached with a thermally conductive adhesive to said interface cover to sense temperature on said interface cover.

11. The heat exchanger module of claim 9, wherein the heat exchanger module is either substantially flat or curved in one or more directions.

12. The heat exchanger module of claim 9, wherein the liquid comprises water.

13. The heat exchanger module of claim 9, wherein the temperature sensors are selected from a group of sensors consisting of: a thermistor, a thermocouple, and a solid state device that outputs a voltage or current proportional to temperature.

14. The heat exchanger module of claim 9, wherein the heat exchanger module either heats or cools the interface cover.

15. The heat exchanger module of claim 14, wherein a rate of heating or cooling the interface cover is controlled.

16. A method of using a heat exchanger module, comprising:
(a) applying a heat exchanger module to a patient, the heat exchanger module comprising:
(i) a flexible substrate, the flexible substrate comprising one or more open channels having a fluid input and fluid output;
(ii) a substrate cover, selected from a group of materials consisting of copper, aluminum, brass, stainless steel, carbon fiber composites and pyrolytic graphite, bonded over the flexible substrate;
(iii) whereby the substrate cover when bonded over the open channels thereby forms closed channels to allow for circulation of a liquid in and out of the channels through said fluid input and fluid output;
(iv) a plurality of thermoelectric coolers bonded to the substrate cover on a reference side of the thermoelectric coolers;
(v) an interface cover bonded with a thermally conductive adhesive to the thermoelectric coolers on a patient side opposite from the reference side;
(vi) a biocompatible elastomeric layer disposed on said interface cover to provide substantially uniform cooling or heating on body tissues to which the heat exchanger module is applied;
(vii) preforming a thermal insulation material with interstitial gaps and device gaps allowing placement of the preformed thermal insulation material over and around the thermoelectric coolers, between said substrate cover and said interface cover, said thermal insulation configured to provide structural support and minimize heat transfer between the substrate cover and said interface cover which would diminish heat transfer efficiency;
(viii) copper squares mounted on said interface cover and/or said substrate cover at locations where each of said plurality of thermoelectric coolers are to be bonded, toward preventing a respective cover from bending around the thermoelectric coolers and for providing enhanced thermal diffusion; and
(ix) one or more temperature sensors disposed within the heat exchanger module attached within one of the interstitial gaps, prior to placement of the preformed thermal insulation material over and around said thermoelectric coolers, to monitor temperature within the interstitial gap, wherein the temperature sensors sense a temperature of the interface cover; and
(b) applying a thermal treatment to the patient by using the heat exchanger module and controlling it through an operator interface for reading and setting temperatures, starting and stopping cooling and heating profiles, defining upper and lower limits for cooling and heating ranges, accessing routines for optimizing PID parameters, accessing routines to program fluid and heat exchange rates, selecting between AC or battery operation, graphically displaying temperature plots, and providing an emergency button which can be accessed to halt the cooling or heating operation of the heat exchange system.

17. The method of using the heat exchanger module of claim 16, wherein the thermal treatment uses a controlled rate of heating.

18. The method of using the heat exchanger module of claim 16, wherein the thermal treatment uses a controlled rate of cooling.

19. The method of using the heat exchanger module of claim 16, wherein the thermal treatment uses a time period of substantially constant heat exchanger module interface cover temperature.

* * * * *